(12) United States Patent
Xing et al.

(10) Patent No.: US 9,897,529 B2
(45) Date of Patent: Feb. 20, 2018

(54) TEST SYSTEM AND TEST METHOD FOR A SIMULATION EXPERIMENT OF GAS HYDRATE IN A POROUS MEDIUM

(71) Applicant: CHINA UNIVERSITY OF PETROLEUM (EAST CHINA), Qingdao (CN)

(72) Inventors: Lanchang Xing, Qingdao (CN); Changling Liu, Qingdao (CN); Qiang Chen, Qingdao (CN); Yanfeng Geng, Qingdao (CN); Chenquan Hua, Qingdao (CN); Yu Qi, Qingdao (CN)

(73) Assignee: CHINA UNIVERSITY OF PETROLEUM (EAST CHINA), Shandong (CN)

( * ) Notice: Subject to any disclaimer, the term of this patent is extended or adjusted under 35 U.S.C. 154(b) by 0 days.

(21) Appl. No.: 15/325,077

(22) PCT Filed: Sep. 12, 2016

(86) PCT No.: PCT/CN2016/098689
§ 371 (c)(1),
(2) Date: Jan. 9, 2017

(87) PCT Pub. No.: WO2017/050142
PCT Pub. Date: Mar. 30, 2017

(65) Prior Publication Data
US 2017/0292904 A1    Oct. 12, 2017

(30) Foreign Application Priority Data

Sep. 23, 2015 (CN) .......................... 2015 1 0613624
Sep. 23, 2015 (CN) .......................... 2015 1 0613731

(51) Int. Cl.
*G01N 15/08*    (2006.01)

(52) U.S. Cl.
CPC ................................. *G01N 15/088* (2013.01)

(58) Field of Classification Search
CPC ...................................................... G01N 15/088
See application file for complete search history.

(56) References Cited

U.S. PATENT DOCUMENTS

| | | | |
|---|---|---|---|
| 2012/0082590 A1* | 4/2012 | Lee .......................... | B01J 3/006 422/109 |
| 2014/0142853 A1 | 5/2014 | Daigle et al. | |

(Continued)

FOREIGN PATENT DOCUMENTS

| | | |
|---|---|---|
| CN | 1614409 A | 5/2005 |
| CN | 101376854 A | 3/2009 |

(Continued)

OTHER PUBLICATIONS

Chen, Qiang et al., "Simulation Experiment of the Relationship between $CO_2$ Hydrate Saturation and Resistance in Porous Media" Natural Gas Geoscience; vol. 20, No. 2; Apr. 2009; pp. 249-253.

(Continued)

*Primary Examiner* — Lisa Caputo
*Assistant Examiner* — Punam Roy
(74) *Attorney, Agent, or Firm* — J.C. Patents

(57) ABSTRACT

The present invention disclosures a test system and test method for a simulation experiment of gas hydrate in a porous medium. The test system comprises a reactor, a sensor system, a hardware interface apparatus and a data processing system; the reactor is used for containing tested medium, the sensor system is mounted inside the reactor, and the sensor system is connected to the data processing system through the hardware interface apparatus; the test method comprises a procedure of experiment and measurement data acquisition, and a procedure of analyzing and processing measurement signals; by establishing of electri- (Continued)

cal model I, acoustic model II and the fused model III, realizing the simulation of the synthesis/decomposition processes of gas hydrate in the deposits in laboratory environment and implementation of the acoustic and electrical parameters combined test, an accurate gas hydrate saturation calculation model can be established at last.

20 Claims, 12 Drawing Sheets

(56) References Cited

U.S. PATENT DOCUMENTS

| | | | | |
|---|---|---|---|---|
| 2015/0205004 | A1* | 7/2015 | Li | E21B 43/00 703/10 |
| 2016/0251943 | A1* | 9/2016 | Li | B01J 12/02 422/162 |
| 2016/0357888 | A1* | 12/2016 | Li | E21B 7/00 |
| 2017/0101853 | A1* | 4/2017 | Gao | G01N 33/225 |

FOREIGN PATENT DOCUMENTS

| | | | | |
|---|---|---|---|---|
| CN | 101377478 | A | * | 3/2009 |
| CN | 201747338 | U | * | 2/2011 |
| CN | 201749071 | U | * | 2/2011 |
| CN | 201749075 | U | * | 2/2011 |
| CN | 201749096 | U | * | 2/2011 |
| CN | 201749097 | U | * | 2/2011 |
| CN | 201749101 | U | * | 2/2011 |
| CN | 201749113 | U | * | 2/2011 |
| CN | 102042942 | A | * | 5/2011 |
| CN | 102042947 | A | * | 5/2011 |
| CN | 102042995 | A | * | 5/2011 |
| CN | 102042996 | A | * | 5/2011 |
| CN | 102043036 | A | * | 5/2011 |
| CN | 101055276 | B | * | 8/2011 |
| CN | 102042930 | B | * | 7/2013 |
| CN | 103323352 | A | | 9/2013 |
| CN | 103424182 | A | | 12/2013 |
| CN | 104215499 | A | * | 12/2014 |
| CN | 104267150 | A | * | 1/2015 |
| CN | 105334546 | A | | 2/2016 |
| CN | 105334547 | A | | 2/2016 |
| CN | 205015491 | U | | 2/2016 |
| JP | 2003-82372 | A | * | 3/2003 |
| KR | 101309358 | B1 | * | 9/2013 |
| KR | 101350340 | B1 | * | 1/2014 |

OTHER PUBLICATIONS

Hu, Gao Wei et al., "Study on Gas Hydrate Formation-dissociation and its Acoustic Responses in Unconsolidated Sands" Geoscience; vol. 22, No. 3; Jun. 2008; pp. 465-474.

Wang, Dong et al., "Acoustic longitudinal properties measurement and temperature and pressure measurement of gas hydrate samples" Science in China Press; vol. 38, No. 8; 2008; pp. 1038-1045.

Chinese International Search Report of corresponding International PCT Application No. PCT/CN2016/098689, dated Oct. 26, 2016.

Chinese Search Report of corresponding Chinese Application No. 201510613624.5, dated Jun. 29, 2016.

Chinese Search Report of corresponding Chinese Application No. 201510613731.8, dated Jun. 12, 2016.

* cited by examiner

TEST SYSTEM AND TEST METHOD FOR A SIMULATION EXPERIMENT OF GAS HYDRATE IN A POROUS MEDIUM

CROSS-REFERENCE TO RELATED APPLICATION

This application is a national phase application of international application No. PCT/CN2016/098689 filed on Sep. 12, 2016, which in turn claims the priority benefits of Chinese application No. 201510613624.5, filed on Sep. 23, 2015 and Chinese application No. 201510613731.8, filed on Sep. 23, 2015. The contents of these prior applications are hereby incorporated by reference in its entirety.

TECHNICAL FIELD

The present invention belongs to the technical field of oil-gas exploration, and particularly relates to a test system and test method for a simulation experiment of gas hydrate in a porous medium.

BACKGROUND OF THE PRESENT INVENTION

To explore natural gas hydrate (referred to as gas hydrate hereinafter), it is required to quantitatively evaluate a natural gas hydrate reservoir. Physical properties of the reservoir may be detected by the geophysical logging technology, and necessary information may be further provided for the quantitative evaluation of the natural gas hydrate reservoir by the logging interpretation technology. At present, for the evaluation of the saturation of gas hydrate, the interpretation is carried out mainly on the basis of the conventional resistivity logging response and acoustic logging response. In comparison to the oil-gas reservoir, the natural gas hydrate reservoir has its particularity, and therefore, before interpretation of the logging response, it is required to establish a logging interpretation model suitable for the natural gas hydrate reservoir. The establishment of a logging interpretation model needs not only to establish a theoretical model, but also to collect lots of logging data and data on rock physical experiments to verify the theoretical model and to optimize parameters. Therefore, lots of rock physical simulation experiments are conducted on the natural gas hydrate to collect high-quality acoustic and electrical test data. This is of irreplaceable significance to the construction of an acoustic and electrical logging interpretation model for the natural gas hydrate reservoir, and further provides a model basis for the application of the acoustic and electrical logging technology in the fine evaluation of the natural gas hydrate reservoir. In addition, in the rock physical simulation experiment process for natural gas hydrate, the deep-going studies on new acoustic and electrical test systems and methods also provide theoretical basis for the development of new logging technologies, and also provide effective technical detection means for the exploration of the law of dynamics of the synthesis/decomposition processes of natural gas hydrate and the law of changes in the spatial distribution state of various phases of substances inside the porous medium.

In the prior test systems and test methods for a simulation experiment of natural gas hydrate, a majority of the involved acoustic and electrical test technologies are implemented separately. For example, CN103323352A discloses "an experimental device and method for tri-axial mechanic-acoustic-electrical synchronous test of natural gas hydrate deposits". The test system and method have the following disadvantages: by the conventional resistivity test technology, the resistance information of a medium to be tested is acquired, but the capacitive reactance information is ignored; only one pair of electrodes is used as the sensors, the tested spatial range is narrow, and information reflecting the anisotropy of the medium to be tested cannot be provided; as the compound of the electrical sensor and the acoustic sensor in a test space is not taken into consideration, the tested object (spatial tested range) of the acoustic sensor is not completely consistent with that of the electrical sensor, so that the information acquired by the two kinds of sensors cannot be unified, and the test data of the two kinds of sensors cannot be combined (fused).

Meanwhile, among methods for calculating the saturation of gas hydrate, in a prior method for calculating the saturation of gas hydrate based on electrical properties of a porous medium containing gas hydrate, the saturation of gas hydrate is estimated mainly by using resistivity data and in combination with the Archie empirical formula. In such methods, the law of changes in the saturation of gas hydrate in the porous medium is described only by using a part of electrical properties (i.e., resistance property) of the porous medium containing gas hydrate. The insufficient depiction of the electrical properties of the medium in the prior methods is one of the important reasons for inducing the calculation error of the saturation of gas hydrate. In addition, the limitation of the Archie empirical formula itself, for example, whether various assumptions provided for the porous medium containing oil, gas or other fluids are suitable or not for the actual situation of gas hydrate, is also a cause for resulting in the error.

SUMMARY OF THE PRESENT INVENTION

The present invention provides a test system for a simulation experiment of gas hydrate in a porous medium and also provides a test method thereof, which can realize the simulation of the synthesis and decomposition processes of natural gas hydrate in the deposits in a laboratory environment, and can implement the combined test of acoustic and electrical parameters.

The technical solutions of the present invention:

A test system for a simulation experiment of gas hydrate in a porous medium, mainly comprising a reactor, a sensor system, a hardware interface apparatus and a data processing system, wherein the reactor is used for containing a medium to be tested, the sensor system is mounted inside the reactor, and the sensor system is connected to the data processing system through the hardware interface apparatus;

the sensor system mainly consists of acoustic sensors, electrical sensors, temperature sensors and pressure sensors;

the hardware interface apparatus comprises:

(1) a waveform generator, configured to generate excitation signals required by the sensor system as inputs to the sensor system;

(2) an acoustic/electrical signal data collection module, an impedance measurement circuit and an ultrasonic excitation signal power amplifier, wherein ultrasonic excitation signals are amplified by the ultrasonic excitation signal power amplifier and then used as inputs to the acoustic sensors, outputs of the acoustic sensors are collected by the acoustic/electrical signal data collection module, and the acoustic/electrical signal data collection module collects signal outputs of the electrical sensors through the impedance measurement circuit;

(3) a temperature collection module and a pressure collection module, which collect signals from the temperature sensors and the pressure sensors, respectively;

(4) a multi-path switching module I, configured to switch the communication between the waveform generator and the sensor system;

(5) a multi-path switching module II, configured to switch the communication between each collection module and the corresponding sensor system; and the data processing system receives and processes data transmitted by each data collection module.

Preferably, in the hardware interface apparatus, a waveform generator can generate excitation signals required by the electrical sensors, and a waveform generator can generate ultrasonic excitation signals required by the acoustic sensors; and the aforementioned waveform generators can be the same waveform generator or different waveform generators.

Preferably, in the hardware interface apparatus, the acoustic/electrical signal data collection module is a compound name of an acoustic signal data collection module and an electrical signal data collection module. It can be a separate acoustic signal data collection module and a separate electrical signal data collection module, or an integrated acoustic/electrical signal data collection module.

Preferably, in the hardware interface apparatus, the multi-path switching module I is mainly configured to switch the communication between the waveform generator and two kinds of sensors which are the acoustic sensors and the electrical sensors. In other words, the multi-path switching module I is mainly configured to switch the communication between the waveform generator and the acoustic sensors or between the waveform generator and the electrical sensors.

Preferably, in the hardware interface apparatus, the multi-path switching module II is mainly configured to switch the communication between the acoustic/electrical signal data collection module and two kinds of sensors which are the acoustic sensors and the electrical sensors. In other words, the multi-path switching module II is mainly configured to switch the communication between the acoustic/electrical signal data collection module and the acoustic sensors or between the acoustic/electrical signal data collection module and the electrical sensors.

Preferably, the data processing system receives and processes, through a remote controller, data transmitted by each data collection module.

Preferably, the reactor is of a coaxial double-cylinder structure, an inner cylinder being coaxially arranged inside an outer cylinder, a top cover being provided at an upper end of the outer cylinder for the purpose of sealing, a filter screen being mounted on a bottom of the reactor; a number of holes are correspondingly provided on the inner cylinder and outer cylinder of the reactor in a same radial plane and on a same diameter of the inner cylinder and the outer cylinder, and the acoustic sensors and the electrical sensors are correspondingly mounted within the holes; a number of holes are provided on the bottom of the reactor, and the temperature sensors are mounted in the holes; two holes are provided on the top cover of the reactor for the purpose of installing (or connecting) a gas pipe II and leading out connecting wires of the sensors, respectively, and a valve and a pressure sensor II are mounted on the gas pipe II; and, two holes are provided on the bottom of the reactor for the purpose of connecting a gas pipe I and a liquid pipe, respectively.

Preferably, acoustic sensors for transmitting and receiving or electrical sensors for transmitting and receiving are provided on the inner cylinder and the outer cylinder on a same diameter.

Specifically, acoustic sensors for transmitting and receiving or electrical sensors for transmitting and receiving are provided on the inner cylinder and the outer cylinder at positions in a same radial plane and on a same diameter extension line.

Or, the acoustic sensor(s) and the electrical sensor(s) form an integrated acoustic/electrical sensor, and acoustic/electrical sensors for transmitting and receiving are provided on the inner cylinder and the outer cylinder on a same diameter.

Specifically, the acoustic sensor(s) and the electrical sensor(s) form an integrated acoustic/electrical sensor, and acoustic/electrical sensors for transmitting and receiving are provided on the inner cylinder and the outer cylinder at positions in a same radial plane and on a same diameter extension line.

Preferably, in an integrated acoustic/electrical sensor, the acoustic sensor is cylindrical and the electrical sensor is ring-shaped; and one end of the acoustic sensor is disposed within the ring of the electrical sensor.

Or, in an integrated acoustic/electrical sensor, the acoustic sensor is cylindrical and the electrical sensor is rectangular; a round hole is formed in the center of the rectangle; and one end of the acoustic sensor is disposed within the round hole of the electrical sensor.

Or, in an integrated acoustic/electrical sensor, the acoustic sensors are cylindrical and the electrical sensor is rectangular; a number of round holes are provided on the rectangle in an axial direction of the reactor; and one end of each of the acoustic sensors is disposed within the round holes of the electrical sensor. In other words, one end of each of the acoustic sensors is disposed within the numbers of round holes of the electrical sensor, respectively.

A test method for a simulation experiment of gas hydrate in a porous medium, mainly comprising: (1) a procedure of experiment and measurement data acquisition, and (2) a procedure of analyzing and processing measurement signals, wherein:

(1) the procedure of experiment and measurement data acquisition comprises:

1) porous medium is filled into a reactor;

2) water and methane gas are fed into the reactor, then the methane gas fully dissolves in the water;

3) the reactor is put in a constant-temperature box, the temperature of the constant-temperature box is set to a certain low temperature to synthesize gas hydrate, and the measurement and control software and the hardware interface apparatus are activated to collect and display data;

4) the temperature of the constant-temperature box is gradually raised at a certain temperature interval to decompose the gas hydrate; when the temperature and pressure in the reactor have become stable after each time of temperature setup, data collection and storage are started; and the data collection and storage is stopped after all data have been stored, wherein, in step 3) and step 4), the data collection process is as follows: the impedance of the medium to be tested is measured by an electrical sensor pair via an interface circuit; the acoustic wave property parameters of the medium to be tested is measured by an acoustic sensor pair; and the temperature and pressure in the reactor are collected by temperature sensors and pressure sensors;

(2) the procedure of analyzing and processing measurement signals comprises:

5) the amount of gas hydrate in the reactor is calculated according to the temperature and pressure values by the following formula:

$$S_H = \frac{\left(\frac{P_1}{Z_1 T_1} - \frac{P_2}{Z_2 T_2}\right) \times \frac{V_G}{R} \times M_H}{\rho_H \times V_V}$$

where $S_H$ is the saturation of gas hydrate in the porous medium; $M_H$ is the molar mass of the gas hydrate (g/mol); $\rho_H$ is the density of the gas hydrate (g/mL); $V_V$ is the volume of the void of the porous medium (L); $V_G$ is the volume of the gas phase in the reactor (L); T is the system temperature (K); $P_1$ is the initial pressure of the system (MPa); $P_2$ is the system pressure in the synthesis/decomposition processes of the gas hydrate (MPa); R is a gas constant which is 8.314 J/(mol·K); and $Z_1$ and $Z_2$ are gas compression factors in the initial state and in each state of the synthesis/decomposition processes, respectively;

6) a model I indicating a quantitative relation between the measurement signals of the electrical sensors and the saturation of gas hydrate is established;

7) a model II indicating a quantitative relation between the measurement signals of the acoustic sensors and the saturation of gas hydrate is established;

8) a model III, indicating a quantitative relation between fused data of the measurement signals of the electrical sensors and the measurement signals of the acoustic sensors, and the saturation of gas hydrate, is established; gas hydrate saturation outputs from the acoustic model (model II) obtained in step 7) and the electrical model (model I) obtained in step 6) are used as inputs for a data fusion algorithm, and the calculated saturation of gas hydrate is used as an output to obtain the gas hydrate saturation model (model III) based on the data fusion of acoustic/electrical measurement signals; and 9) the model, indicating the quantitative relation between fused data of the measurement signals of the electrical sensors and the measurement signals of the acoustic sensors, and the saturation of gas hydrate, is used:

the impedance of the medium to be tested is measured by an electrical sensor pair via an interface circuit, and gas hydrate saturation values I are obtained by the reverse deduction of the model I obtained in step 6);

the medium to be tested are measured by an acoustic sensor pair through pulse signals, and gas hydrate saturation values II are obtained by the reverse deduction of the model II obtained in step 7); and a value is obtained by fusion algorithm from gas hydrate saturation values (I and II), from which a final gas hydrate saturation value III is obtained by the reverse deduction of the model III obtained in step 8).

Preferably, in step 3), the certain low temperature is selected from 0° C. to 5° C.; and in step 4), the certain temperature interval is a temperature interval from 0.5° C. to 2.5° C.

Apparently, in step 5), it can be seen from the formula that the amount of gas hydrate in the reactor refers to the saturation of gas hydrate in the porous medium in the reactor.

Preferably, the step of establishing the model I indicating a quantitative relation between the measurement signals of the electrical sensors and the saturation of gas hydrate in step 6) is as follows:

impedance values at a series of frequency points within a certain frequency range and in each state are acquired by the electrical sensors, frequency points having an impedance amplitude changed significantly with the saturation are selected as characteristic frequency points, and the measured impedance values are preprocessed;

complex resistivity at each of the characteristic frequency points is calculated according to the definition of the complex resistivity and in combination with the structure and size of the reactor;

the frequency dispersion of the impedance and the frequency dispersion of the complex resistivity are calculated, respectively;

the above obtained frequency dispersion parameters are respectively performed polynomial fitting with the calculated saturation of gas hydrate, so as to obtain a gas hydrate saturation model based on the frequency dispersion of the impedance at the characteristic frequency points and a gas hydrate saturation model based on the frequency dispersion of the complex resistivity at the characteristic frequency points, respectively;

the impedance values of all characteristic frequency points and the complex resistivity values calculated according to the impedance values are used as inputs for a multi-dimensional nonlinear mapping, and the calculated saturation of gas hydrate is used as an output of the multi-dimensional nonlinear mapping, so as to eventually obtain an electrical property fusion model of the saturation of gas hydrate by a corresponding learning algorithm; and the above obtained three models are the model I.

Specifically, the said each state refers to a stable state obtained every time when the temperature and pressure in the reactor become stable in step 4), the said a certain frequency range is selected from 0.01 Hz to 100 MHz, and the said a series of frequency points refer to points selected from the certain frequency range according to actual requirements.

Preferably, in the step of establishing the model I, the impedance values acquired by the electrical sensors need to be preprocessed, and the preprocessing includes filtering and characteristic frequency points selection.

Preferably, the step of establishing the model II indicating a quantitative relation between the measurement signals of the acoustic sensors and the saturation of gas hydrate in step 7) is as follows:

the acquired acoustic waveforms are preprocessed, including filtering, calculating the acoustic wave velocity, acquiring the acoustic wave amplitude and acquiring the acoustic wave frequency;

property parameters of acoustic waves under different gas hydrate saturation conditions are acquired;

the above acoustic wave property parameters are respectively performed polynomial fitting with the calculated saturation of gas hydrate, so as to obtain a gas hydrate saturation model based on the acoustic wave velocity, a gas hydrate saturation model based on the acoustic wave amplitude and a gas hydrate saturation model based on the acoustic wave frequency, respectively;

the above three acoustic wave property parameters are used as inputs for a multi-dimensional nonlinear mapping, the calculated saturation of gas hydrate is used as an output of the multi-dimensional nonlinear mapping, so as to eventually obtain an acoustic property fusion model of the saturation of gas hydrate by a corresponding learning algorithm; and the above obtained four models are the model II.

Preferably, during the data collection in step 3) and step 4), a pair of sensors is switched to work by a multi-path switching module at each measurement.

Preferably, during the data collection in step 3) and step 4), for the acoustic sensors, the acoustic sensors are excited by a coded excitation technology.

Preferably, an ultrasonic excitation signal obtained by the coded excitation technology is a single-frequency carrier pulse signal, a frequency-modulated pulse signal, a coded pulse signal, a pulse train signal or a phase encoded continuous-wave signal.

Preferably, during the data collection in step 3) and step 4), for the acoustic sensors, the ultrasonic excitation signal excites an acoustic sensor by using a continuous-wave signal or a single-pulse signal.

Preferably, during the data collection in step 3) and step 4), for the electrical sensors, the excitation signal performs frequency sweeping excitation on every test point within a certain frequency range by a voltage signal having sine waveforms with a certain amplitude, frequency and DC bias, where the amplitude is 0.01 V to 5V and the frequency is 0.01 Hz to 100 MHz.

Specifically, the excitation signal performs frequency sweeping excitation on every test point within a certain frequency range of 0.01 Hz to 100 MHz by a voltage signal having sine waveforms with an amplitude of 0.01 V to 5V, a frequency of 0.01 Hz to 100 MHz and a DC bias of −5V to +5V Preferably, the ultrasonic excitation signal is fed into the acoustic sensors after power amplification.

Compared with the prior art, the present application has the following beneficial effects.

(1) In the test system, different combinations of a plurality of sensors are realized by designing a novel reactor and by arranging the sensors in an array, so that the sensors have a broader coverage and higher reliability and robustness. Accordingly, multiple kinds of related and consistent information can be acquired for a same object to be tested or a same state, and the acquired information is larger in amount and has a higher degree of confidence.

(2) The test system employs an architecture of virtual instruments, in which a computer acts as the core and software-based and modularized instruments are also equipped. The modularized instrument system adopts the standard data bus technology (for example, PXI bus), and the system supports flexible configurations and has high integration level and reliability. The developed graphical measurement and control software can flexibly configure hardware apparatuses as required, control the hardware apparatuses (instruments, board cards, etc.) and realize high-speed and high-precision data collection and processing. A friendly human-computer interaction interface supports the functions of flexibly setting parameters, preprocessing data and waveforms, real-time displaying, saving, etc.

(3) In the test method, by performing different levels of fusion on the measurement data of the sensors and by adopting different fusion system structures and fusion algorithms, different data fusion models can be established. On this basis, information contained in the measurement data of the acoustic and electrical sensors can be mined more deeply, so that more useful information is provided for the establishment of gas hydrate saturation calculation models and the exploration of the law of dynamics in the synthesis/decomposition processes of gas hydrate and the law of changes in the spatial distribution state of various phases of substances in the porous medium.

(4) The test method of the present application uses the concepts of multi-sensor combination and data fusion in the modern information field for reference, and is proposed mainly according to the characteristics of natural gas hydrate.

(5) In this test method, the information about the natural saturation of gas hydrate is acquired based on the frequency dispersion property parameters of electrical parameters (for example, the frequency dispersion of complex resistivity) of the porous medium containing natural gas hydrate. Compared with the existing method for calculating saturation of gas hydrate based on electrical properties of a medium, in the present application, the frequency dispersion property parameters of electrical parameters (for example, the frequency dispersion of complex resistivity) not only contain information about both resistivity and dielectric constant of a medium, but also can depict the property that both resistivity and dielectric constant change with the test frequency. Therefore, electrical properties of the medium containing natural gas hydrate can be described more comprehensively and deeply, and richer information is provided for improving the calculation precision of the natural saturation of gas hydrate.

(6) In the test method, the acoustic sensors are excited by the flexible coded excitation technology. Compared with the currently widely used single-pulse and one-time excitation way, this test method has the advantages of better noise suppression performance, lower amplitude of the required signals, and flexibly adjustable frequency and waveform of the excitation signals, the signal-to-noise ratio received by the acoustic sensors on the receiving side is higher, the contained information is richer, and more high-quality information is provided for the subsequent data analysis and processing.

(7) By this system and the corresponding test method, physical simulation experiments related to natural gas hydrate can be efficiently carried out, acoustic and electrical test parameter data containing rich information can be acquired, and accurate natural gas hydrate saturation calculation models can be established, so that effective detection technical means are provided for the exploration of the law of dynamics in the synthesis/decomposition processes of natural gas hydrate and the law of changes in the spatial distribution state of various phases of substances in the porous medium, and a theoretical basis is provided for the development of new logging technologies (including logging instruments and corresponding data interpretation models and methods).

Figure 1:
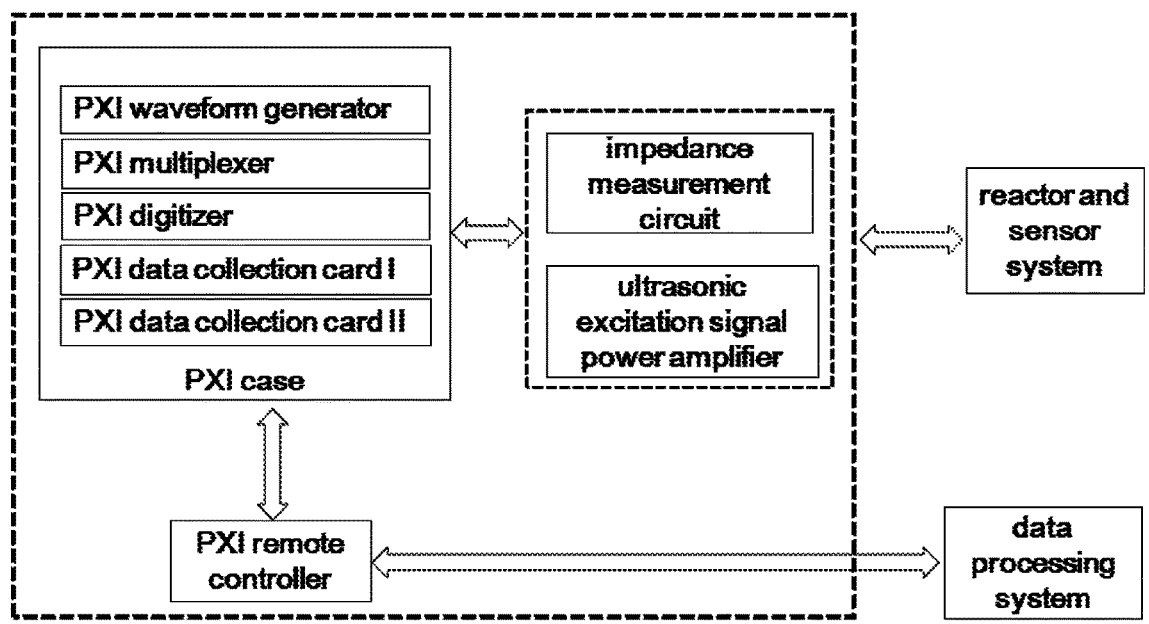
FIG. 1 is a diagram of a test system for a simulation experiment of gas hydrate in a porous medium according to Embodiment 1.

where: 1: outer cylinder; 2: inner cylinder; 3: top cover; 4: filter screen; 5: acoustic sensor; 6: electrical sensor; 7: temperature sensor; 8: pressure sensor I; 9: gas pipe I; 10: liquid pipe; 11: flow control valve; 12: pressure sensor III; 13: stop valve; 14: three-way connector; 15: filter valve; 16: pressure sensor II; and 17: gas pipe II.

DETAILED DESCRIPTION OF THE PRESENT INVENTION

1. Test System of the Present Application

The test system for a simulation experiment of gas hydrate in a porous medium is mainly used for measuring, in real time, acoustic parameters, electrical parameters, temperature and pressure of a porous medium system containing natural gas hydrate. This system mainly comprises four parts, a reactor, a sensor system (acoustic sensors, electrical sensors, temperature sensors and pressure sensors), a hardware interface apparatus, and a software system (measurement and control software and a monitoring computer). The hardware interface apparatus and the software system employ an architecture of a virtual instrument, in which a computer acts as the core and software-based and modularized instruments are also equipped.

(1) Reactor

The reactor provides a place for the synthesis and decomposition of natural gas hydrate and also provides support for the mounting of sensors. The reactor of the present application is of a coaxial double-cylinder structure.

The reactor can be divided into five parts, i.e., an outer cylinder, a detachable inner cylinder, a detachable top cover, a detachable filter screen and other attachments used for sealing and connection. As an implementation, the outer cylinder further comprises a cylinder bottom and a detachable lining, and there may be no lining on the bottom (cylinder bottom) of the outer cylinder.

The outer cylinder of the reactor is made of corrosion-resistant and high-pressure-resistant metal material which can be stainless steel or high-strength aluminum alloy. The lining of the outer cylinder is made of insulating material, for example, polytetrafluoroethylene. The inner cylinder can be made of metal material, for example, stainless steel or high-strength aluminum alloy, or can be made of insulating material, for example, polytetrafluoroethylene.

The inner cylinder is of a detachable structure, and grooves for positioning the relative position of the inner cylinder and the outer cylinder are formed on the bottom of the outer cylinder and the top cover. A number of holes are provided on the top cover and the bottom of the outer cylinder, and these holes are used as passageways for feeding and discharging a reactant gas and liquid, for example, methane gas, distilled water, saline water, etc., or passageways for leading out signal wires, or used for mounting acoustic sensors, electrical sensors, temperature sensors and pressure sensors.

The filter screen plays a role of uniformly distributing the gas and liquid entering the reactor, so that the gas and liquid entering the reactor are uniformly distributed in the whole reaction space.

(2) Sensor System and Arrangement Thereof

The sensor system mainly consists of acoustic sensors, electrical sensors, temperature sensors and pressure sensors.

The acoustic sensors can be ultrasonic transducers used for transmitting and receiving ultrasonic wave signals, respectively. According to different measured acoustic parameters and parameter measurement methods, the type, structure and array arrangement of the acoustic sensors can be different.

The electrical sensors can be point electrodes, rectangular electrodes or annular electrodes made of metal sheets. The electrode material can be copper, platinum or titanium alloy with good electrical conductivity. The structure and array arrangement of the electrical sensors depend on the measured electrical parameters and the adopted measurement methods.

The temperature sensors can be resistance temperature detectors, thermocouples and semiconductor thermistors and are used for measuring the temperature at each position in the reactor. To ensure the accuracy of the temperature measurement, the size of the sensors and the thermal inertia should be reduced as much as possible and the response speed should be increased as much as possible. Armored resistance temperature detectors or thermocouples can be used.

The sensors can be arranged in the following ways.

Figure 2:
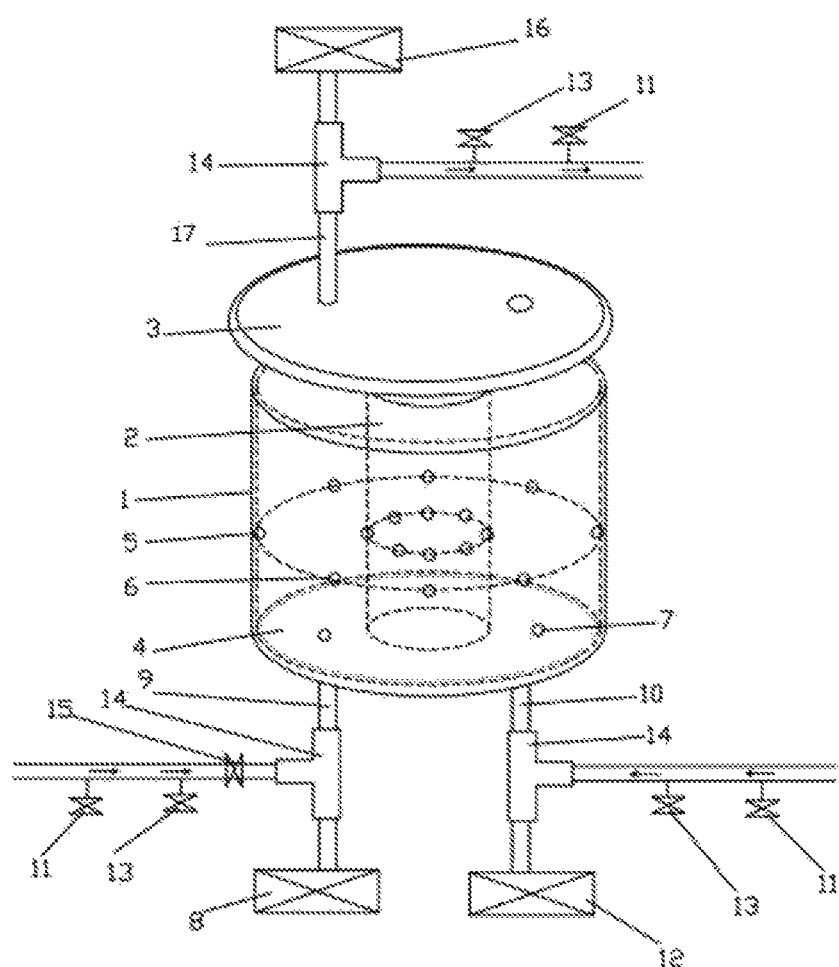
FIG. 2 is a structural diagram of a reactor.

To indicate directions and positions, by taking the reactor body as a reference object in the present application, the up-and-down direction of the reactor body shown in FIG. 2 is an axial direction, the direction vertical to the axial direction is a radial direction, and the plane of the radial direction is a radial plane. This reference position is used merely for describing a relative space structure and not intended to limit the protection scope of the present application.

Figure 13:
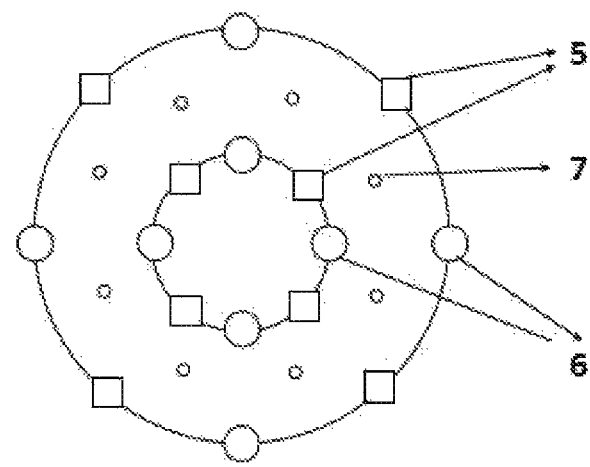
FIG. 13 is a cross-sectional diagram of positions where independent acoustic sensors and electrical sensors are mounted.

The acoustic sensors and the electrical sensors are mounted on sides of both the outer cylinder and the inner cylinder of the reactor, and one layer of sensors are arranged in the axial direction. The sensors are located in a same radial plane which is also called a cross-section or a horizontal plane. The sensors are arranged in the following way: two opposite sensors on the inner cylinder and the outer cylinder being of a same type are called a sensor pair, for instance, they are both electrodes as the electrical sensors or both ultrasonic transducers as the acoustic sensors. The sensor pair mentioned in the present application mostly refers to this case. As an implementation, sensor pairs are uniformly arranged in a circumferential direction (the central angle between any two adjacent sensor pairs is the same), and an included angle (central angle) between two adjacent sensor pairs can be set as 45 degrees, as shown in FIG. 13.

As the optimal positions of each sensor pair, two sensors of a same type are arranged on the inner cylinder and the outer cylinder in a same radial plane and on a same diameter extension line.

Apparently, any one sensor is mounted on the inner side of the outer cylinder or on the outer side of the inner cylinder in order to ensure that the sensor can measure parameters of gas hydrate in the porous medium.

The ultrasonic transducers can be ultrasonic transducers for transmitting, ultrasonic transducers for receiving or ultrasonic transducers for both transmitting and receiving. The operating mode of the ultrasonic transducers can be single-transmitting single-receiving or single-transmitting multi-receiving. The sensors on the inner cylinder can be used for transmitting, while the sensors on the outer cylinder are used for receiving; or, the sensors on the outer cylinder can be used for transmitting, while the sensors on the inner cylinder are used for receiving.

The temperature sensors, such as resistance temperature detectors, are inserted from the cylinder bottom. The temperature sensing portions of the temperature sensors are located in a same radial plane as the above acoustic sensors and the electrical sensors, and located between respective diameters of two adjacent sensor pairs, without influencing the signal transmission between the electrical sensor pair and that of the acoustic sensor pair. Thus, the temperature sensors cannot be located between two electrical sensors or two acoustic sensors forming a sensor pair.

As an implementation, one or more layers of acoustic sensor pairs and electrical sensor pairs can be arranged in the axial direction of the reactor, and the number of layers is determined according to the actual size of the reactor and the measurement requirements;

There may be one or more pairs, for example, two pairs, four pairs, eight pairs, sixteen pairs, of acoustic sensor pairs and electrical sensor pairs in each radial plane. The number of pairs is determined according to the actual size of the reactor and the measurement requirements.

The acoustic sensors and the electrical sensors can be independent sensors or integrated sensors.

When the acoustic sensors and the electrical sensors are independent sensors, in a same radial plane, the acoustic sensor pairs and the electrical sensor pairs can be arranged at different angles. As an implementation, the acoustic sensor pairs and the electrical sensor pairs are arranged circumferentially in a staggered manner.

When the acoustic sensor(s) and the electrical sensor(s) are integrated sensors, two opposite integrated sensors form an integrated sensor pair. In a same radial plane, an integrated sensor pair is arranged on the inner cylinder and the outer cylinder at a same angle. In other words, the positions of one integrated sensor pair on the inner cylinder and the outer cylinder are in a same radial plane and on a same diameter extension line.

Figure 15:
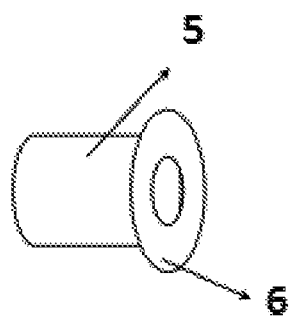
FIG. 15 is a structural diagram of an integrated acoustic/electrical sensor according to Embodiment 2.
Figure 16:
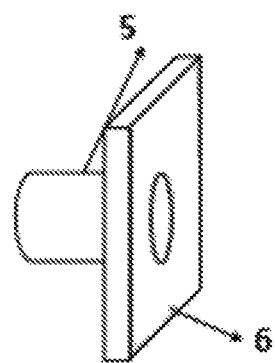
FIG. 16 is a structural diagram of an integrated acoustic/electrical sensor according to Embodiment 3.
Figure 17:
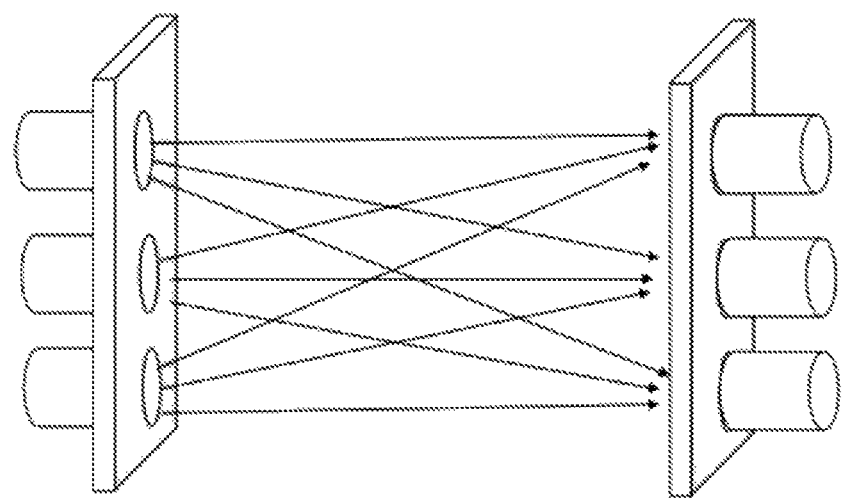
FIG. 17 is a structural diagram of an integrated acoustic/electrical sensor according to Embodiment 4 and a schematic diagram of an operation mode of single-transmitting multi-receiving.

When the acoustic sensor(s) and the electrical sensor(s) are integrated sensors (also referred to as acoustic/electrical sensors), as an implementation, the acoustic sensor is cylindrical, the electrical sensor is ring-shaped, and the cylindrical acoustic sensor is arranged in the ring-shaped hollow portion, as shown in FIG. 15. As another implementation, the acoustic sensor(s) is/are cylindrical, the electrical sensor is rectangular, and hole(s) having a same area as the cross-sectional area of the acoustic sensors is/are formed in the centers of the rectangles. When the electrical sensor is rectangular, edges in the axial direction are long edges, and one or more acoustic sensors can be mounted along the direction of the long edges, so that the operating mode of single-transmitting single-receiving or single-transmitting multi-receiving can be realized. As shown in FIG. 16, one electrical sensor and one acoustic sensor form an integrated sensor; however, as shown in FIG. 17, one electrical sensor and three acoustic sensors form an integrated sensor.

As an implementation, the inner cylinder can be taken out directly and is not used, and a space for synthesizing and decomposing gas hydrate in the reactor is a cylindrical space (when the inner cylinder is used, the space for synthesizing and decomposing gas hydrate in the reactor is annular). At this time, the opposite sensors on the outer cylinder form a corresponding sensor pair, i.e., an acoustic sensor pair or an electrical sensor pair. The acoustic sensors on the outer cylinder can be acoustic sensors for both transmitting and receiving.

The number of sensors, whether the inner cylinder is used or not and the pairing way of sensors depend on the parameters to be measured and the principle of parameter measurement methods. The more the sensors are, the more the acquired information is, and the higher the requirements for the information and signal processing are. If there are more sensors, more holes need to be provided on the wall of the high-pressure reactor, and the more holes will reduce the strength of the wall of the reactor and increase the difficulty of sealing. Therefore, whether the inner cylinder is used or not, the number of sensors and the pairing way are determined on the basis of a comprehensive consideration of these factors.

(3) Hardware Interface Apparatus

The hardware interface apparatus is mainly used for generating excitation signals required by the sensors and collecting output signals from the sensors. The selection of the hardware interface apparatus needs to fully consider the type and number of the sensors, the form and intensity (amplitude or power) of the excitation signals, the stability and extendibility of the apparatus, and a necessary interface circuit module (drive circuit module) can be developed voluntarily as required.

The sensors mainly refer to acoustic sensors and electrical sensors because both of them need excitation signals. For example, the excitation signals for the acoustic sensors can be ultrasonic excitation signals.

The hardware interface apparatus is mainly divided into two parts, i.e., an acoustic test interface apparatus and an electrical test interface apparatus.

Figure 3:
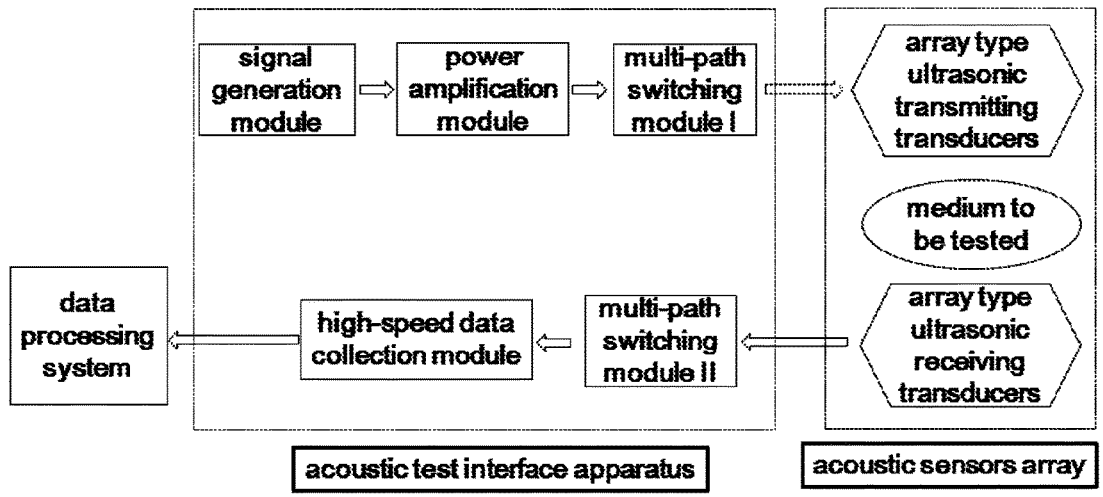
FIG. 3 is a flowchart of signal transmission of an acoustic test interface apparatus.

As shown in FIG. 3, the acoustic test interface apparatus mainly comprises a signal generation module, a power amplification module, a high-speed data collection module and multi-path switching modules, wherein the power amplification module is selectively used depending on whether the actual intensity of the excitation signals is matched with the intensity of signals required by the acoustic sensors. Specifically, the signal generation module can be a waveform generator, the power amplification module can be an ultrasonic excitation signal power amplifier, the high-speed data collection module can be an acoustic signal data collection module, and the multi-path switching modules include a multi-path switching module I and a multi-path switching module II.

Figure 4:
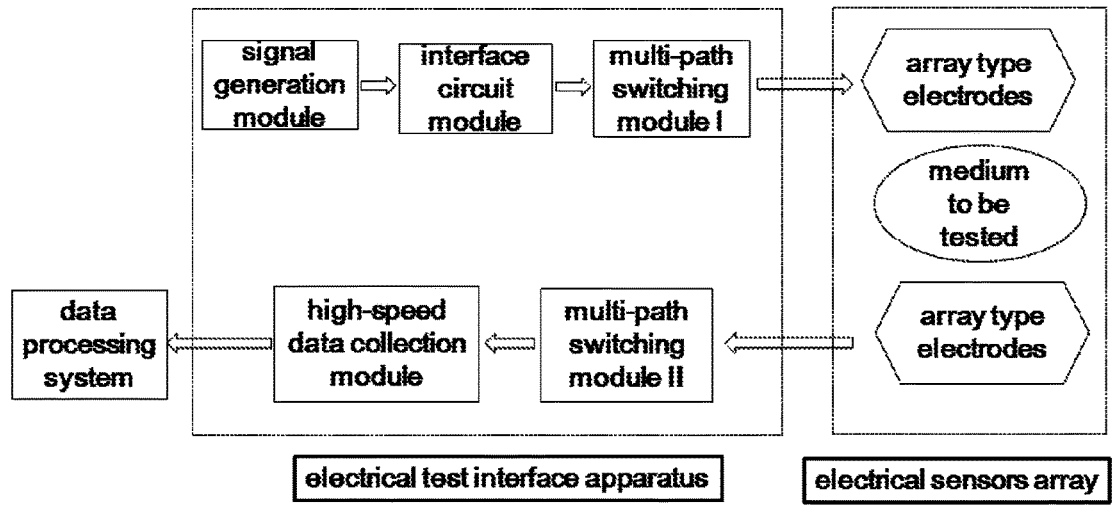
FIG. 4 is a flowchart of signal transmission of an electrical test interface apparatus.

As shown in FIG. 4, the electrical test interface apparatus mainly comprises a signal generation module, an interface circuit module, a high-speed data collection module and multi-path switching modules. Specifically, the signal generation module can be a waveform generator, the interface circuit module can be an impedance measurement circuit, the high-speed data collection module can be an electrical signal data collection module, and the multi-path switching modules include a multi-path switching module I and a multi-path switching module II.

For the acoustic test interface apparatus and the electrical test interface apparatus, the signal generation modules of the both are used for generating excitation signals for driving the acoustic sensors or the electrical sensors, and major signal waveforms are sine waveforms of different frequencies, square waveforms of different frequencies, pulse signals of different frequencies and various flexibly customized coded excitation signals. The signal generation modules of the both can be a same waveform generator or different waveform generators. The specific selection is determined according to the waveform, amplitude, frequency, power and other parameters of the output signals of the adopted waveform generators.

For the acoustic test interface apparatus and the electrical test interface apparatus, the high-speed data collection modules of the both are collectively called an acoustic/electrical signal data collection module. The acoustic/electrical signal data collection module can be an independent acoustic signal data collection module and an independent electrical signal data collection module, or can be an integrated acoustic/electrical signal data collection module. The specific selection is determined according to the number of input ports of the data collection module. The collection of electrical signals needs at least two input ports, while the collection of acoustic signals needs at least one port.

For the acoustic test interface apparatus and the electrical test interface apparatus, the multi-path switching modules of the both can be a same multi-path switching module or different multi-path switching modules. The specific selection is determined according to the number of channels of the multi-path switching modules, the maximum tolerable voltage, the maximum tolerable current, bandwidth and other parameters. The electrical signals have higher requirements on the bandwidth (at least 100 MHz), and the acoustic signals requires that the tolerable voltage is at least 500 V and the tolerable current is at least 0.5 A. The number of channels is required by the both, and is consistent with (at least equal to) the number of sensor pairs. However, the number of channels is generally greater than the number of sensor pairs, to ensure the extendibility and the timely adjustment after one channel is damaged.

The multi-path switching modules can ensure that only one sensor pair is operating at each measurement. In other words, only one acoustic sensor pair or electrical sensor pair is operating. Such an arrangement can effectively eliminate the interference between the sensor pairs. In addition, the use of the multi-path switching modules enables the signal generation module and the high-speed data collection module to be multiplexed between a plurality of sensor pairs, so that the hardware cost is greatly reduced.

The hardware interface apparatus further comprises a temperature collection module and a pressure collection module, which collect signals from the temperature sensors and the pressure sensors, respectively.

(4) Software System (Measurement and Control Software and Monitoring Computer)

Figure 10:
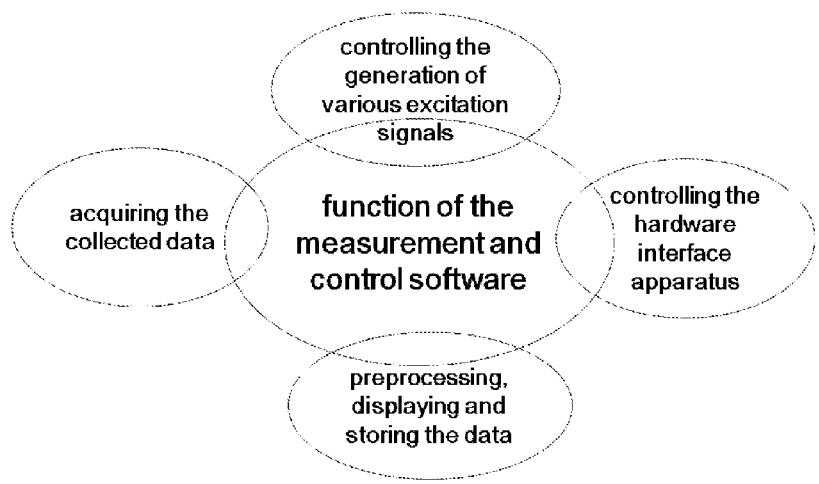
FIG. 10 is a functional diagram of measurement and control software.

The software system, i.e., the data processing system described hereinbefore, is used for receiving and processing data transmitted by the data collection modules. The data collection modules mainly refer to the acoustic/electrical signal data collection module, the temperature collection module and the pressure collection module. The software system (data processing system) mainly comprises a measurement and control software and a monitoring computer, wherein, The measurement and control software is mainly used for realizing the following functions: controlling the generation of various excitation signals, controlling the hardware interface apparatus, acquiring the collected data, and preprocessing, displaying and storing the data, as shown in FIG. 10. The measurement and control software can be developed based on a graphical programming software platform LabVIEW, or can be realized through hybrid programming by using VC or VB, and Matlab.

The control of the hardware interface apparatus by the measurement and control software mainly refers to the control to the multi-path switching modules, the high-speed data collection module and the signal generation module. The successive excitation of the sensor array and the data collection can be realized by controlling the multi-path switching modules. The control to the high-speed data collection module mainly comprises selection of channels, configuration of the collection frequency, the program-controlling amplifier gain (amplification factor), the cache and the like.

The data is processed before displayed and stored, for example, digital filtering, parameter calculation, etc. The data display mainly comprises: excitation signals (time-domain and frequency-domain waveforms and numerical values), acoustic wave measurement signals (time-domain and frequency-domain waveforms and numerical values), acoustic wave amplitude attenuation, acoustic wave propagation velocity, impedance values (amplitudes, phase angles, real parts, and imaginary parts), impedance charts (Nyquist charts, Bode diagrams, etc.). The data is stored as a text file or a binary file, for a deeper analysis in the later stage. The algorithms for the further data analysis will be specifically described in the test method section, and the specific implementation of the algorithms is realized by powerful scientific calculation software Matlab, or realized by C or C++ language programming.

The monitoring computer can be an industrial personal computer, an ordinary desktop computer (personal PC), a laptop computer (portable computer) or an embedded computer, etc.

2. Test Method of the Present Application

With regard to the above system, a test method for a simulation experiment of gas hydrate in a porous medium is provided. This method is an electrical/acoustic combined test method and comprises two parts, i.e., a procedure of experiment and measurement data acquisition, and a procedure of analyzing and processing measurement signals. The test method is mainly specific to a porous medium containing gas hydrate in an annular space, but is also suitable for a case where the inner cylinder is taken out.

(1) Procedure of Experiment and Measurement Data Acquisition

1) The top cover of the reactor is opened, and a porous medium (for example, quartz sand, natural sea sand, etc.) is filled into an annular space between the inner cylinder and the outer cylinder of the reactor. The height of the filled porous medium exceeds the location of the acoustic sensors and the electrical sensors, and a certain gas storage space is reserved between the porous medium and the sealed top cover.

2) Water required for synthesizing gas hydrate is slowly injected from the bottom of the reactor until the porous medium is water-saturated, and the top cover is put on the reactor and then fixed and sealed. Methane gas is slowly fed from the bottom of the reactor until reaching a set pressure, for example, 7 MPa to 20 MPa, preferably 10 MPa. The reactor stands for 24 hours to fully dissolve the methane gas in water, and observation is performed on whether there is leakage.

3) Synthesis process of gas hydrate: the reactor is put into a constant-temperature box, the measurement and control software and the hardware interface apparatus are activated to collect and display data, the temperature of the constant-temperature box is set to a certain low temperature, for example, 0° C. to 5° C., preferably 1° C., and the data is stored while starting to decrease the temperature. By observing temperature and pressure curves, it is determined whether the synthesis process of gas hydrate has been finished, and data storage is stopped if the synthesis process of gas hydrate has been finished (note: data collection and displaying are not stopped).

4) Decomposition process of gas hydrate: the set temperature of the constant-temperature box is gradually raised at a certain temperature interval, for example, 0.5° C. to 2.5° C., preferably 0.5° C. The state point obtained when the temperature and pressure in the reactor become stable after each time of temperature setup is a relatively stable state point, and then the data storage is started. After all the data is stored, the data storage is stopped, and the set temperature of the constant-temperature box is raised by the temperature interval. After the temperature and pressure in the reactor become stable, the data storage is started; and the data storage is stopped after all the data is stored. The above process is repeated until the gas hydrate is decomposed completely.

It is to be noted that, the decomposition process of gas hydrate is mainly performed within a range of 0° C. to 10° C.; and there has been a very small amount of gas hydrate remaining in the reactor after the temperature exceeds 10° C., so the subsequently decomposed amount is very small. However, in the practical operation process, the temperature range of the decomposition process is generally set as 0° C. to room temperature (25° C.), wherein, in the decomposition process at a temperature from 0° C. to 10° C., the amount of gas hydrate decomposed is large, and the properties of the porous medium containing the gas hydrate change rapidly, so state points to be collected (i.e., state points obtained when the temperature and pressure in the reactor become stable after each time of temperature setup, as described above) are relatively dense, and thus a certain temperature within the range of 0.5° C. to 2.5° C. (preferably 0.5° C.) is selected as a temperature interval to perform the test and data collection; and, in the decomposition process at a temperature from 10° C. to the room temperature, the decomposed amount of gas hydrate is small, and the properties of the porous medium containing the gas hydrate change slowly, so a larger temperature interval, for example, 3° C. to 7° C., preferably 4° C., can be selected to perform the test and data collection.

In the experiment process, the measurement data is acquired only by operating a corresponding button on the panel of the measurement and control software, for example, by clicking "start to collect", "start to store", etc., and the specific function of the buttons are realized by the measurement and control software.

A physical process of acquiring measurement data of the acoustic sensors and the electrical sensors will be described below.

For the electrical sensors, two electrodes located separately on the inner cylinder and the outer cylinder form an electrode pair, and the excitation signals can be user-set sine waves (voltage signals) having a certain amplitude, frequency and DC bias. The typical amplitude is 0.01 V to 5 V, and the frequency is 0.01 Hz to 100 MHz. As an implementation, a DC bias of −5 V to +5 V is selected on this basis. Frequency sweeping excitation is performed within the frequency range when each stable state point is tested (the tested state points are called test points hereinafter), impedance measurement is performed on the medium to be tested through the interface circuit, and the data collection modules perform high-speed and high-precision sampling on the measurement signals under the control of the software, so that the impedances of the medium to be tested between two electrodes at different test frequencies are acquired. If the inner cylinder is not used, two opposite electrodes on the outer cylinder form an electrode pair, and the same data acquisition method as above can be used.

For the acoustic sensors, two ultrasonic transducers located separately on the inner cylinder and the outer cylinder form a sensor pair. The ultrasonic transducers on the outer cylinder can be used for transmitting, while the ultrasonic transducers on the inner cylinder are used for receiving; or, the ultrasonic transducers on the inter cylinder can be used for transmitting, while the ultrasonic transducers on the outer cylinder are used for receiving. The ultrasonic excitation signals can be continuous-wave signals, for example, sine wave continuous signals; or, can be single-pulse signals; or, can also be specially coded signals, for example, single-frequency carrier pulse signals, frequency-modulated pulse signals, coded pulse signals, pulse train signals, phase encoded continuous-wave signals and so on. The single-pulse signals have the advantages of short duration, high emission frequency, high resolution, etc., but the average power of the signals is still low in the case where their peaks are already close to the maximum allowable value. The specially coded signals (e.g., coded pulse signals) have the advantages of ensuring high average power and high emission frequency, so that the signal-to-noise ratio can be improved without reducing the resolution. It is to be noted that, the excitation signals can be somewhat amplified in power by a power amplifier and then transmitted to the ultrasonic transmitting transducers, but the external power amplifier can be omitted if power amplification modules are embedded into the ultrasonic transducers. For each test point, i.e., each stable state of the medium to be tested, a certain number (e.g., 1 to 100) of ultrasonic tests are performed. If a transmitting transducer transmits coded pulse signals for several times at a certain time interval (e.g., an interval selected from 1 ms to 1 s), a receiving transducer receives corresponding ultrasonic signals, and the data collection modules perform high-speed and high-precision sampling on the output signals of both the transmitting transducer and the receiving transducer under the control of the software, so that paired transmitting waveforms and receiving waveforms are acquired. The number of ultrasonic tests and the time interval for signal transmission are adjusted according to the amount of data actually to be measured and the precision, and are not certain specific data.

It is to be further noted that, the waveforms, amplitudes, frequencies and other parameters of the excitation signals for the acoustic sensors and the electrical sensors can be flexibly adjusted by the measurement and control software. In other words, for each test point, excitation signals having different waveforms, amplitudes and frequencies can be used sequentially to acquire more measurement information, so that a large amount of basic data and rich information are provided for the subsequent signal processing.

(2) Procedure of Analyzing and Processing Measurement Signals

As an implementation, the analysis and processing of the measurement signals includes two parts, i.e., online real-time preprocessing and offline processing. The online processing is mainly realized by the measurement and control software as described above, and the algorithms for the offline data processing can be realized by scientific calculation software Matlab.

5) The synthesis/decomposition processes of the gas hydrate are determined by the change curves of the temperature and pressure, and the amount of gas hydrate, i.e., the saturation of gas hydrate, in the reaction system is calculated according to the temperature and pressure values. The saturation of gas hydrate is calculated by the following formula:

$$S_H = \frac{\left(\frac{P_1}{Z_1 T_1} - \frac{P_2}{Z_2 T_2}\right) \times \frac{V_G}{R} \times M_H}{\rho_H \times V_V}$$

where $S_H$ is the saturation of gas hydrate in the porous medium; $M_H$ is the molar mass of the gas hydrate (122.02 g/mol); $\rho_H$ is the density of the gas hydrate (0.91 g/mL); $V_V$ is the volume of the void of the porous medium (L); $V_G$ is the volume of the gas phase in the reactor (L); T is the system temperature (K); $P_1$ is the initial pressure of the system (MPa); $P_2$ is the system pressure in the synthesis/decomposition processes of the gas hydrate (MPa); R is a gas constant which is 8.314 J/(mol·K); and $Z_1$ and $Z_2$ are gas compression factors in the initial state and in each state of the synthesis/decomposition processes, respectively.

The saturation of gas hydrate obtained by the calculation formula is called calculated saturation of gas hydrate hereinafter. Apparently, in this formula, the test states of $P_1$, $T_1$ and $Z_1$ are the same, and the test states of $P_2$, $T_2$ and $Z_2$ are the same; and, $P_1$, $T_1$ and $Z_1$ are parameters in the initial state, and $P_2$, $T_2$ and $Z_2$ are parameters in the synthesis/decomposition processes of the gas hydrate, wherein the initial state refers to a state when "water and methane gas are fed into the reactor, then the methane gas is fully dissolved in the water" in step 2).

6) The measurement signals of the electrical sensors are processed and gas hydrate saturation models (model I) are established.

Before modeling, concepts related to the impedance are introduced first for further use. The impedance is used for describing the inhibition effect to the current in a circuit having resistance, inductance and capacitance. In the present application, the porous medium containing gas hydrate is regarded as a "circuit". The impedance value is a value for evaluating the impedance and is a complex number, where the real part is called resistance while the imaginary part is called reactance. The impedance amplitude is a numerical value obtained by modulo operation of the impedance value.

Impedance values at a series of frequency points within the frequency range in each state are acquired by the electrical sensors. The change of the frequency values of the frequency points from small to large can be linear or logarithmic, which is determined according to the actual test range. If the frequency range is small, the linear change can be selected; however, if the frequency range is large, that is, the maximum value of the range is at least 1000 times of the minimum value, the logarithmic change can be selected. If the linear change is selected, the interval between the frequency values of the frequency points can be selected from 1 Hz to 1 kHz. If the logarithmic change is selected, the frequency values of the frequency points can be a power of 10 with an integer exponent, for example, the frequency values are $10^0$ Hz, $10^1$ Hz, $10^2$ Hz and the like.

In the first step, the measured impedance values are preprocessed, specifically comprising filtering and characteristic frequency points selection. Wherein, the filtering can be performed by designing a digital filter (e.g., Butterworth filter) by Matlab, and the principle for characteristic frequency points selection is that frequency points having an impedance amplitude changed significantly with the saturation of gas hydrate are selected.

In the second step, the complex resistivity at each of the characteristic frequency points is calculated according to the definition of the complex resistivity (similar to the common resistivity calculation method) and in combination with the structure and size of the reactor.

In the third step, the frequency dispersion of the impedance and the frequency dispersion of the complex resistivity are calculated, respectively, where the frequency dispersion can be the following four forms of parameters (called frequency dispersion parameters): (the impedance (or complex resistivity) value at a high frequency point—the impedance (or complex resistivity) value at a low frequency point)/the impedance (or complex resistivity) value at the high frequency point, (the impedance (or complex resistivity) value at a high frequency point—the impedance (or complex resistivity) value at a low frequency point)/the impedance (or complex resistivity) value at the low frequency point, the impedance (or complex resistivity) value at a high frequency point/the impedance (or complex resistivity) value at a low frequency point), and the impedance (or complex resistivity) value at a low frequency point)/the impedance (or complex resistivity) value at a high frequency point.

In the fourth step, a polynomial fitting (single-input and single-output) is performed between the obtained frequency dispersion parameters respectively of the impedance and the calculated saturation of gas hydrate, and a polynomial fitting (single-input and single-output) is performed between the obtained frequency dispersion parameters respectively of the complex resistivity and the calculated saturation of gas hydrate, so as to obtain a gas hydrate saturation model based on the frequency dispersion of the impedance at the characteristic frequency points and a gas hydrate saturation model based on the frequency dispersion of the complex resistivity of the frequency points, respectively. The impedance data of only two relatively low and high frequency points are utilized in the third step, but a series of characteristic frequency points are actually selected in the preprocessing process. The impedance values of all the characteristic frequency points selected in the preprocessing process, and the complex resistivity values calculated according to the impedance values, are used as inputs for a multi-dimensional nonlinear mapping (multi-input), and the calculated saturation of gas hydrate is used as an output of the multi-dimensional nonlinear mapping (single-output), so as to eventually obtain an electrical property fusion model of the saturation of gas hydrate by a corresponding learning algorithm. The learning algorithm can be a machine learning algorithm. It is to be noted that, the impedance values and the complex resistivity values are not directly used as inputs for the nonlinear mapping, and instead, a characteristic vector is first acquired by a "characteristic extraction" step. The "characteristic extraction" step can be realized by principal component analysis method, and the obtained characteristic vector is used as the input for the nonlinear mapping. This nonlinear mapping can be a machine learning model, for example, an artificial neural network, a support vector machine and others. In accordance with different machine learning models, corresponding learning algorithms are selected, for example, a BP learning algorithm is selected for the neural network.

Figure 6:
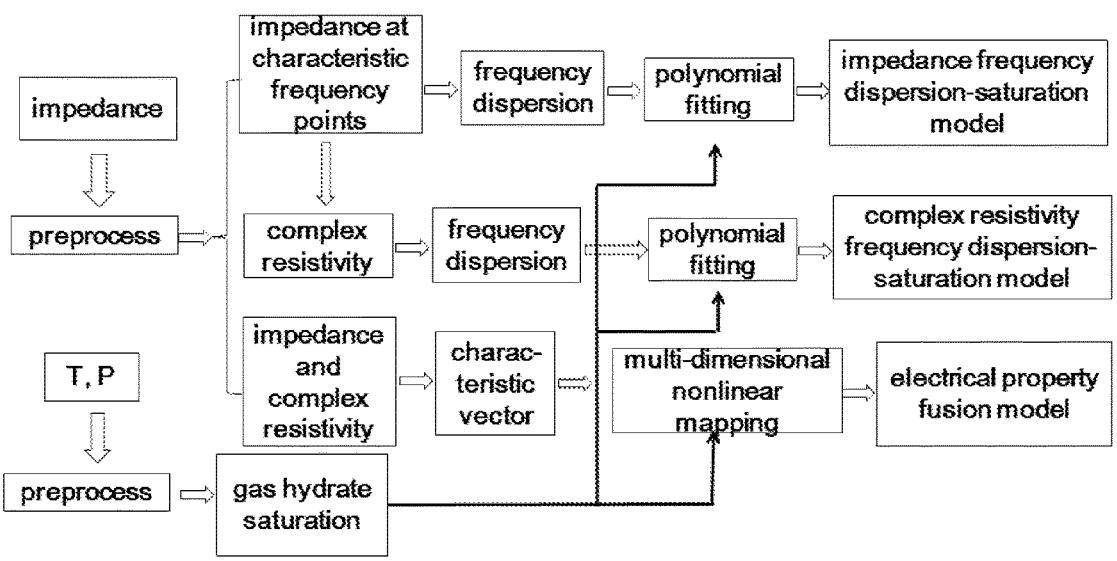
FIG. 6 is a flowchart of processing electrical test signals and establishing saturation models.

By the above steps, the analysis and processing of the electrical measurement data (signals) are realized. In this way, a quantitative relation between the saturation of gas hydrate and the electrical parameters is obtained, which is used to analyze the dynamic processes of the synthesis/decomposition of the gas hydrate. Meanwhile, three gas hydrate saturation calculation models can be established, that is, the gas hydrate saturation model based on the frequency dispersion of the impedance of the characteristic points (the impedance frequency dispersion-saturation model in FIG. 6), the gas hydrate saturation model based on the frequency dispersion of the complex resistivity of the characteristic points (the complex resistivity frequency dispersion-saturation model in FIG. 6), and the electrical property fusion model (as shown in FIG. 6)). The three models are called electrical models, i.e., model I. The saturation of the gas hydrate can be calculated in the subsequent experiment process by the models by using electrical measurement data, and a basis is provided for establishing an electrical logging interpretation model.

7) The measurement signals of the acoustic sensors are processed and gas hydrate saturation models (model II) are established.

Data on acoustic waveforms transmitted by the ultrasonic transducers and data on acoustic waveforms received by the ultrasonic transducers are acquired through the acoustic sensors in each state and under the condition of a series of coded excitation signals.

In the first step, the acquired acoustic waveforms are processed, comprising filtering, calculating the acoustic wave velocity, acquiring the acoustic wave amplitude and acquiring the acoustic wave frequency. A digital filter (e.g., Butterworth filter) can be designed by Matlab. Calculating the acoustic wave velocity includes calculating a velocity of longitudinal waves and a velocity of transverse waves, which is done by identifying the arrival time of the first wave of the longitudinal waves and that of the transverse waves in the waveforms and in combination with the size of the reactor. The acoustic wave amplitude refers to the maximum amplitude of corresponding longitudinal waves and transverse waves in the waveforms. The acoustic wave frequency refers to a dominant frequency of the acoustic waves and is obtained by a certain signal processing method, for example, a frequency spectrum obtained by fast Fourier transform, a time-frequency spectrum obtained by a short-time Fourier transform, Gabor transform or wavelet transform and so on. The frequency point corresponding to the maximum frequency spectrum amplitude is the dominant frequency.

In the second step, property parameters of the acoustic waves in different states (different gas hydrate saturation conditions) can be acquired based on the results of calculation in the first step, specifically: (the acoustic wave velocity at a different saturation–the acoustic wave velocity when the saturation of gas hydrate is zero)/the acoustic wave velocity when the saturation of gas hydrate is zero, (the acoustic wave amplitude at a different saturation–the acoustic wave amplitude when the saturation of gas hydrate is zero)/the acoustic wave amplitude when the saturation of gas hydrate is zero, and (the acoustic wave dominant frequency at a different saturation–the acoustic wave dominant frequency when the saturation of gas hydrate is zero)/the acoustic wave dominant frequency when the saturation of gas hydrate is zero.

In the third step, a polynomial fitting (single-input and single-output) is performed between the obtained acoustic wave property parameter of the acoustic wave velocity and the calculated saturation of gas hydrate, a polynomial fitting (single-input and single-output) is performed between the obtained acoustic wave property parameter of the acoustic wave amplitude and the calculated saturation of gas hydrate, and a polynomial fitting (single-input and single-output) is performed between the obtained acoustic wave property parameter of the acoustic wave frequency and the calculated saturation of gas hydrate, so as to obtain a gas hydrate saturation model based on the acoustic wave velocity, a gas hydrate saturation model based on the acoustic wave amplitude and a gas hydrate saturation model based on the acoustic wave frequency, respectively. The three acoustic wave property parameters are used as inputs for a multi-dimensional nonlinear mapping (multi-input), the calculated saturation of gas hydrate is used as an output of the multi-dimensional nonlinear mapping (single-output), so as to eventually obtain an acoustic property fusion model of the saturation of gas hydrate by a corresponding learning algorithm. The learning algorithm can be a machine learning algorithm. It is to be noted that, the three acoustic wave property parameters are not directly used as inputs for the nonlinear mapping, and instead, a characteristic vector is first acquired by a "characteristic extraction" step. The "characteristic extraction" step can be realized by principal component analysis method, and the obtained characteristic vector is used as the input for the nonlinear mapping. This nonlinear mapping can be a machine learning model, for example, an artificial neural network, a support vector machine and so on. In accordance with different machine learning models, corresponding learning algorithms are selected, for example, a BP learning algorithm is selected for the neural network.

Figure 7:
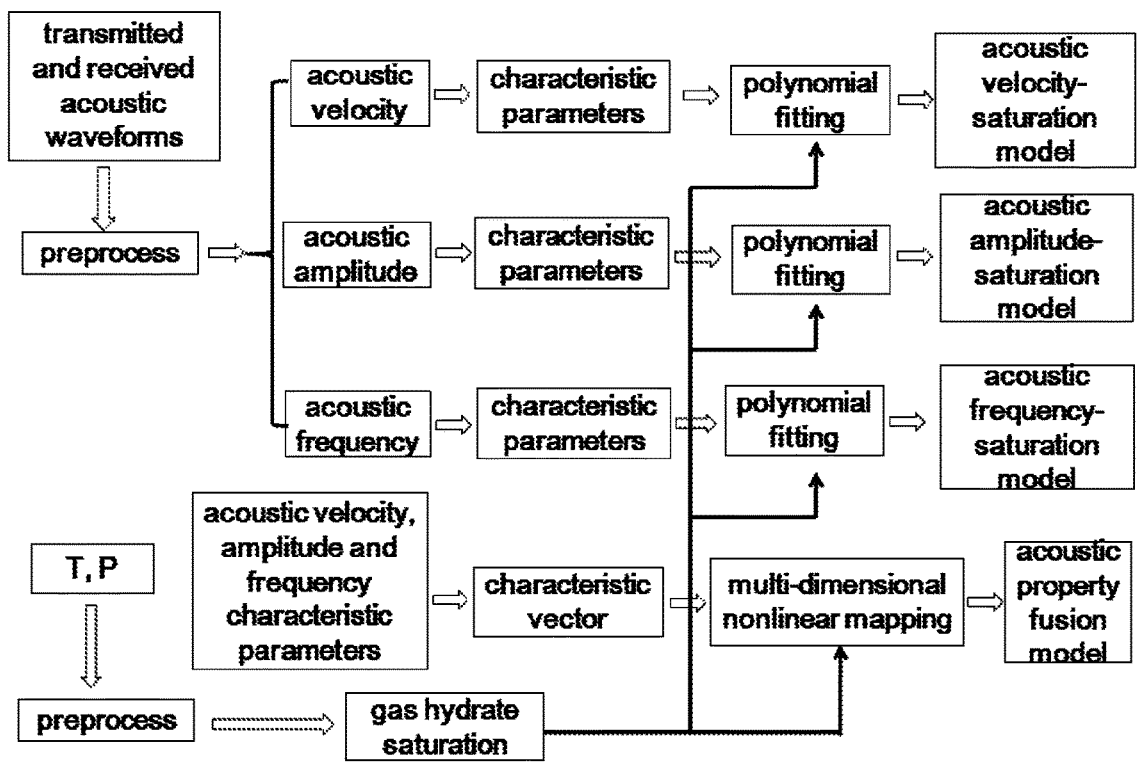
FIG. 7 is a flowchart of processing acoustic test signals and establishing saturation models.

By the above steps, the analysis and processing of the acoustic measurement data are realized. In this way, a quantitative relation between the saturation of gas hydrate and the acoustic parameters is obtained, which is used to analyze the dynamic processes of the synthesis/decomposition of the gas hydrate. Meanwhile, four gas hydrate saturation calculation models can be established, that is, the gas hydrate saturation model based on the acoustic wave velocity (the acoustic velocity-saturation model in FIG. 7), the gas hydrate saturation model based on the acoustic wave amplitude (the acoustic amplitude-saturation model in FIG. 7), the gas hydrate saturation model based on the acoustic wave frequency (the acoustic frequency-saturation model in FIG. 7) and the acoustic property fusion model (as shown in FIG. 7)). The four models are called acoustic models, i.e., model II. The saturation of the gas hydrate can be calculated in the subsequent experiment process by the models by using acoustic test data, and a basis is provided for establishing an acoustic logging interpretation model.

8) A gas hydrate saturation model (model III) based on the data fusion of electrical/acoustic measurement signals is established and applied.

The establishment of the gas hydrate saturation model based on the data fusion of electrical/acoustic measurement signals (i.e., electrical/acoustic property fusion model) is based on the gas hydrate saturation models which are established with respect to the acoustic and electrical measurement signals and which are also called the acoustic sub-model (model II) and the electrical sub-model (model I)

hereinafter. The outputs of the models are combined (fused) by a data fusion algorithm, so as to obtain a final gas hydrate saturation output value of the model.

Figure 8:
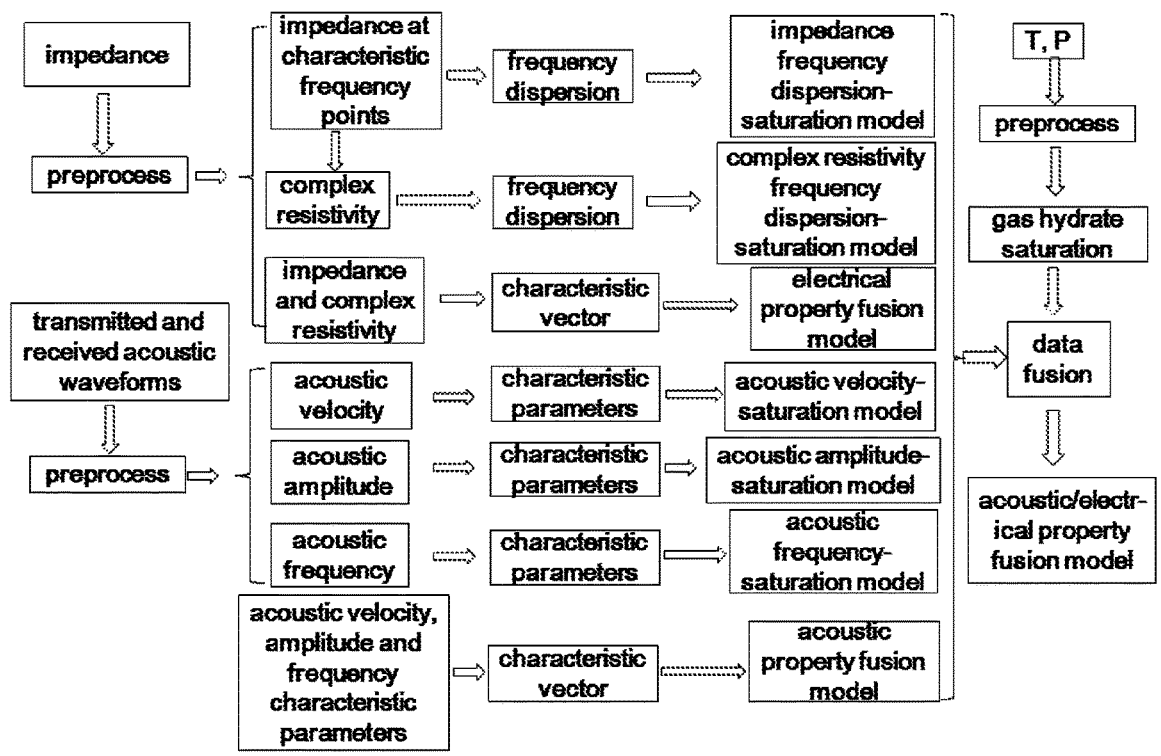
FIG. 8 is a flowchart of collectively processing electrical and acoustic test signals and establishing a saturation model.

When the gas hydrate saturation model based on the data fusion of electrical/acoustic measurement signals is established, the gas hydrate saturation outputs of the acoustic sub-model and the electrical sub-model are used as inputs for the data fusion algorithm (multi-input), and the calculated saturation of gas hydrate is used as an output (single-output). The fusion algorithm can be a random algorithm, for example, weighted averaging, Kalman filtering, multi-Bayes estimation, D-S evidence reasoning, Bayes statistics, etc.; or, can be an artificially intelligent algorithm, for example, fuzzy logic, neural network, rough set theory, expert system, etc. Training and parameter correction are performed on the data fusion algorithm by using the calculated saturation of gas hydrate, so that the gas hydrate saturation model based on the data fusion of acoustic/electrical measurement signals (i.e., model III) can be obtained (as shown in FIG. 8).

When the gas hydrate saturation model based on the data fusion of electrical/acoustic measurement signals is applied, the measurement signals of the electrical sensors and the acoustic sensors are analyzed and processed by the method as described above, and the value of the saturation of gas hydrate can be eventually output from the acoustic/electrical property fusion model. Specifically, an electrical sensor pair is used to measure impedance of the medium to be tested via an interface circuit module, and gas hydrate saturation values I are obtained by the reverse deduction of the model I obtained in step 6); an acoustic sensor pair is used to measure acoustic property parameters of the medium to be tested by using pulse signals as excitation signals, and gas hydrate saturation values II are obtained by the reverse deduction of the model II obtained in step 7); and, a value is obtained by fusing the gas hydrate saturation values (I and II), from which a final gas hydrate saturation value III is obtained by the reverse deduction of the model III obtained in step 8).

The present application will be described below in more details with reference to the accompanying drawings and embodiments. In the present application, the accompanying drawings and the embodiments are merely for describing the implementations and not intended to limit the scope of the present application. Various transformations and improvements made to the technical solutions of the present application by a person of ordinary skill in the art without departing from the design spirit of the present application shall fall into the protection scope defined by the claims of the present application. In an embodiment, any apparatus or module once involving a model number shall be interpreted as explaining this embodiment, but this embodiment is not limited to this apparatus or module, and other apparatuses or modules capable of realizing the same function as this apparatus or module can be used.

Embodiment 1

Figure 5:
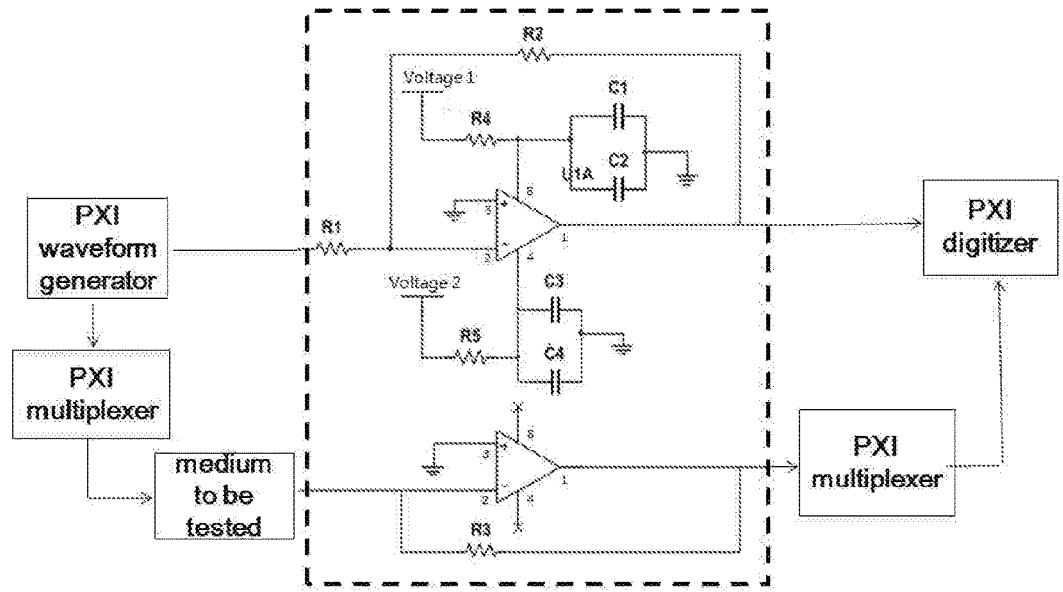
FIG. 5 is a connection diagram of an electrical test interface circuit.

As shown in FIG. 1 and FIG. 2, the present invention provides a test system for a simulation experiment of gas hydrate in a porous medium, mainly comprising a reactor, a sensor system, a hardware interface apparatus and a data processing system, wherein the reactor is used for containing a medium to be tested, the sensor system is mounted inside the reactor, and the sensor system is connected to the data processing system through the hardware interface apparatus;

the sensor system mainly consists of acoustic sensors 5, electrical sensors 6, temperature sensors 7 and pressure sensors (8, 12, 16);

the hardware interface apparatus comprises:

a waveform generator, configured to generate excitation signals required by the sensor system as inputs to the sensor system, where a PXI waveform generator is used in this embodiment;

an acoustic/electrical signal data collection module, an impedance measurement circuit and an ultrasonic excitation signal power amplifier, the acoustic/electrical signal data collection module being a PXI digitizer in this embodiment, wherein ultrasonic excitation signals from the PXI waveform generator is amplified by the ultrasonic excitation signal power amplifier and then used as inputs to the acoustic sensors on a transmitting side, outputs of the acoustic sensors on a receiving side are collected by the acoustic/electrical signal data collection module, the acoustic/electrical signal data collection module collects signal outputs of the electrical sensors through the impedance measurement circuit, and the impedance measurement circuit is an interface circuit module shown in FIG. 4 and the part in a dashed box shown in FIG. 5;

a temperature collection module and a pressure collection module, collect signals from the temperature sensors and the pressure sensors, respectively, where, in this embodiment, the temperature collection module is a PXI data collection card I and the pressure collection module is a PXI data collection card II;

a multi-path switching module I, configured to switch the communication between the waveform generator and the sensor system, where, in this embodiment, the multi-path switching module I is a PXI multiplexer; and a multi-path switching module II, configured to switch the communication between each collection module and the corresponding sensor system, where, in this embodiment, the multi-path switching module I and the multi-path switching module II share a same PXI multiplexer; and the data processing system receives and processes data transmitted by each data collection module, where this function is realized by a monitoring computer and measurement and control software in this embodiment.

The reactor comprises an outer cylinder 1, an inner cylinder 2, a top cover 3 and a filter screen 4, which all are of a detachable structure, and further comprises other attachments used for sealing and connection. The outer cylinder 1 comprises a wall and detachable lining, and has no lining on its bottom.

The outer cylinder 1 of the reactor is made of high-strength aluminum alloy, the lining of the outer cylinder 1 is made of polytetrafluoroethylene material, and the inner cylinder 2 is made of polytetrafluoroethylene material. The withstand pressure of the reactor is designed as 20 MPa.

The inner cylinder 2 is of a detachable structure, and grooves (not shown) for positioning the relative position of the inner cylinder 2 and the outer cylinder 1 are formed on the bottom of the outer cylinder 1 and the top cover 3. A number of holes are provided on the top cover 3 and the bottom of the outer cylinder 1, and these holes are used as passageways for feeding and discharging a reactant gas and liquid, for example, methane gas, distilled water, saline water and so on, or passageways for leading out signal wires, or used for mounting acoustic sensors, electrical sensors, temperature sensors and pressure sensors.

The structure of the reactor is shown in FIG. 2. The reactor is of a coaxial double-cylinder structure. The inner cylinder 2 is coaxially arranged inside the outer cylinder 1, the top cover 3 is arranged at the upper end of the outer cylinder 1 for purpose of sealing, and the filter screen 4 is mounted on the bottom of the reactor. A number of holes are correspondingly provided inside the inner cylinder 2 and outer cylinder 1 of the reactor in a same radial plane and on a same diameter extension line of the inner cylinder and the outer cylinder, and the acoustic sensors 5 and the electrical sensors 6 are correspondingly mounted within the holes. A number of holes are provided on the bottom of the reactor, and the temperature sensors 7 are mounted in the holes. Two holes are provided on the top cover 3 of the reactor for the purpose of receiving a gas pipe II 17 and leading out connecting wires of the sensors, respectively. A flow control valve 11 and a pressure sensor II 16 are mounted on the gas pipe II 17. The gas pipe II 17 is used for discharging gas.

Ten holes are provided on the bottom of the reactor. Among the ten holes, eight holes are used for mounting the temperature sensors and the temperature sensors are armored resistance temperature detectors Pt100 in this embodiment, one hole is used for mounting a gas pipe I 9, and one hole is used for mounting a liquid pipe 10. A flow control valve 11 and a pressure sensor I 8 are provided on the gas pipe I 9; a flow control valve 11 and a pressure sensor III 12 are provided on the liquid pipe 10. A 500-mesh ceramic or stainless filter screen 4 is mounted on the bottom of the reactor.

As shown in FIG. 13, a layer of acoustic sensors 5 and electrical sensors 6 mounted in the reactor. Eight holes for mounting the sensors are provided on sides of each of the inner cylinder 2 and the outer cylinder 1 of the reactor. Paired acoustic sensors 5 used for transmitting and receiving or paired electrical sensors 6 used for transmitting and receiving are arranged on the inner cylinder 2 and the inner cylinder 1 in a same radial plane and on a same diameter extension line.

The filter screen 4 plays a role of uniformly distributing the gas and liquid entering the reactor, so that the gas and liquid entering the reactor are uniformly distributed in the whole reaction space.

Temperature sensing portions of the temperature sensors and acoustic/electrical sensors array are in a same radial plane (the temperature sensing portions of the temperature sensors are not shown in FIG. 2).

The connection relationship between the hardware interface apparatus and other components is shown in FIG. 1. In this embodiment, the hardware interface apparatus adopts mainly modular instruments based on a PXI bus. The hardware interface apparatus mainly consists of a PXI case, a PXI remote controller, a PXI waveform generator, a PXI multiplexer (a multi-path switching module, a multi-path switch), a PXI digitizer, a PXI data collection card I, a PXI data collection card II, an interface circuit, a power supply and other attachments.

The PXI modular instruments (board card) are inserted into card slots of the PXI case, so that the size of the hardware apparatus can be reduced greatly while maintaining the high performance of the system. The PXI remote controller is connected to a remote monitoring computer, so that the control to the modules in the case can be realized at 7 m at most. In this embodiment, the data processing system receives and processes data transmitted by the data collection modules through the PXI remote controller, and also control all modular instruments in the PXI case to work normally. The monitoring computer is an industrial personal computer with excellent performance and high stability.

Among the PXI modular instruments, the PXI waveform generator can be an arbitrary waveform generator, with a 16-bit resolution, a maximum sampling rate of 1 GS/s, an onboard memory of 1G to 8G and a maximum amplitude of 20 V (the output range is −10V to 10V), for generating excitation signals for the acoustic sensors and the electrical sensors, wherein the PXI-waveform generator can realize customized coded excitation signals by programming according to actual requirements.

The PXI digitizer can be used as an acoustic/electrical signal data collection module, and has a real-time sampling rate of 500 MS/s, four 16-bit resolution channels for synchronous sampling and a 500 MHz bandwidth with a de-noising and anti-aliasing filter. The PXI digitizer realizes the high-speed and high-precision A/D conversion and sampling of impedance measurement signals and ultrasonic signals of the medium to be tested.

The multi-path switching module can be a PXI multiplexer. The multiplexer can be used for 32 paths of switching and can be flexibly configured by the measurement and control software.

The temperature collection module can be a PXI data collection card I. This collection card is especial for the temperature measurement of a Pt100 resistance temperature detector, has 30 collection channels and a sampling rate of at most 200 S/s for each channel in a high-speed mode, and provides a sampling rate of at most 2 S/s and a typical measurement precision of 0.060 in a high-resolution mode.

The PXI data collection card II is a high-voltage analog input module (i.e., the above-described pressure collection module), and provides the integrated data collection and signal conditioning for the high voltage measurement so as to realize the measurement of pressure.

FIG. 5 shows an interface circuit between the waveform signal generator and the electrical sensors (electrodes). The excitation signals are simultaneously applied to the standard resistor and the object to be tested (the porous medium between two electrodes). The interface circuit conditions the excitation signals, and high-speed simultaneous data collection is performed on the conditioned signals by the PXI digitizer.

Embodiment 2

Figure 14:
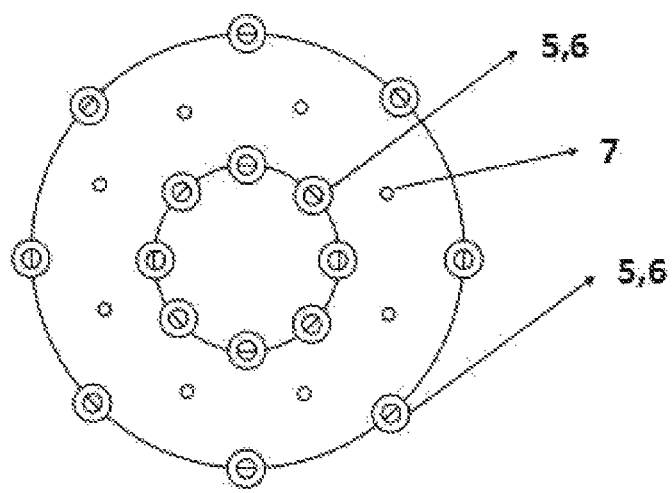
FIG. 14 is a cross-sectional diagram of positions where integrated acoustic/electrical sensors are mounted, according to Embodiment 2.

A difference between this embodiment and Embodiment 1 lies in that the acoustic sensors and the electrical sensors are integrated acoustic/electrical sensors in this embodiment. As shown in FIG. 14, the acoustic sensors and the electrical sensors are integrated acoustic/electrical sensors, and the acoustic/electrical sensors used for transmitting and receiving are arranged on the inner cylinder and the outer cylinder on a same diameter extension line.

For one integrated acoustic/electrical sensor, the acoustic sensor is cylindrical and the electrical sensor is ring-shaped, and one end of the acoustic sensor is disposed within the rings of the electrical sensor, as shown in FIG. 15.

Embodiment 3

A difference between this embodiment and Embodiment 1 and Embodiment 2 lies in that the acoustic sensors and the electrical sensors are integrated acoustic/electrical sensors in this embodiment; as shown in FIG. 16, for one integrated acoustic/electrical sensor, the acoustic sensor is cylindrical and the electrical sensor is rectangular, a round hole is formed in center of the rectangle, and one end of the acoustic sensor is disposed within the round hole of the electrical sensor.

Embodiment 4

A difference between this embodiment and Embodiments 1 to 3 lies in that the acoustic sensors and the electrical sensors are integrated acoustic/electrical sensors in this embodiment; for the integrated acoustic/electrical sensors, the acoustic sensors are cylindrical and the electrical sensors are rectangular, a number of round holes are formed on the rectangles in the axial direction of the reactor, and one end of each of the acoustic sensors are disposed within the round holes of the electrical sensors, as shown in FIG. 17.

Embodiment 5

The test method is implemented by the following operating process.

The top cover 3 of the reactor is opened, and natural sea sands are filled into the annular space between the inner cylinder 2 and the outer cylinder 1 of the reactor. The height of the sea sands is 5 cm over the radial plane of the acoustic/electrical sensors array, and a certain gas storage space having a height of 5 cm is reserved between the sea sand surface and the top cover 3.

A three-way connector 14 is mounted on the liquid pipe 10. Liquid is fed from one end of the three-way connector through a flow control valve 11 and a stop valve 13, and the other end of the three-way connector is connected to a pressure sensor III 12. The stop valve 13 of the liquid pipe 10 on the bottom is opened, saline water having a mass percentage of 3.5% is slowly injected from the liquid pipe 10 on the bottom of the reactor through the flow control valve 11 until the sea sands is water-saturated, the top cover 3 is put on the reactor, fixed and sealed, then the stop valve 13 is closed. The gas pipe I 9 is connected to a hole on the bottom of the reactor through a three-way connector 14 and a filter valve 15. One end of the three-way connector 14 is connected to a high-pressure gas cylinder through a flow control valve 11 and a stop valve 13, while the other end thereof is connected to the pressure sensor I 8. Methane gas is slowly fed from the gas pipe I 9 on the bottom of the reactor and then passes through the flow control valve 11 until the set pressure 10 MPa is reached. The reactor stands for 24 hours to fully dissolve the methane gas into water, and observation is performed on whether there is leakage.

The reactor is put into a constant-temperature box, the measurement and control software and the hardware interface apparatus are activated to collect and display data, the temperature of the constant-temperature box is set to 1□, and the data is stored while starting to decrease the temperature. The temperature and pressure curves are observed to judge whether the synthesis process of gas hydrate has been finished, and data storage is stopped if the synthesis process of gas hydrate has been finished (note: data collection and displaying are not stopped).

Figure 11:
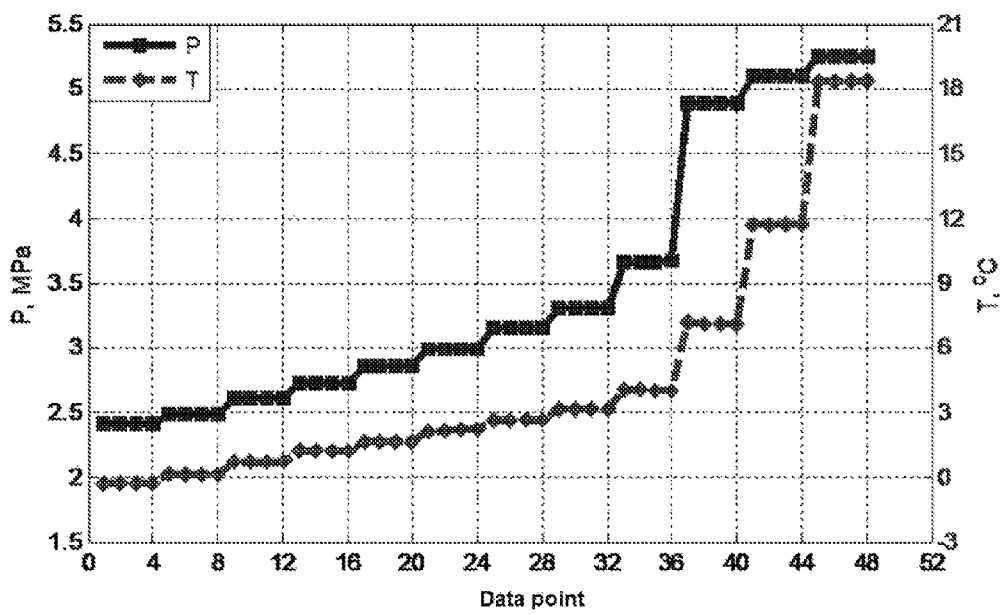
FIG. 11 shows test points at which impedance spectroscopy data is collected actually.

The temperature of the constant-temperature box is gradually raised at a temperature interval of 0.5□. The data storage is started when the temperature and pressure in the reactor become stable after each time of temperature setup. After all the data is stored, the data storage is stopped, and the temperature of the constant-temperature box is raised by 0.5□. After the temperature and pressure in the reactor become stable, the data storage is started; and the data storage is stopped after all the data is stored. The above process is repeated until the gas hydrate is decomposed completely. FIG. 11 shows temperature and pressure curves in the decomposition process of gas hydrate while raising the temperature, wherein data points are test points where the impedance is actually collected.

Two points need to be noted.

For the electrical sensors, two electrodes located separately on the inner cylinder and the outer cylinder form an electrode pair, and the excitation signals are user-set sine waves (voltage signals) having a certain amplitude, frequency and DC bias. In this embodiment, the amplitude is 5 V, the frequency range is 100 Hz to 10 MHz, and the DC bias is 0V. Ten cycles of sine wave excitation are performed for each test point, and frequency sweeping excitation is performed within the test frequency range with an interval of 100 Hz, for example, 100 Hz, 200 Hz, 300 Hz, . . . , 10 MHz are used as test frequency points.

For the acoustic sensors, two ultrasonic transducers located separately on the inner cylinder and the outer cylinder form a single-transmitting and single-receiving sensor pair. In this embodiment, the ultrasonic transducers on the outer cylinder are used for transmitting, while the ultrasonic transducers on the inner cylinder are used for receiving. The ultrasonic excitation signals are linear frequency-modulated signals. The central frequency of the frequency-modulated signals is consistent with that of the transmitting transducers and is 500 kHz, the bandwidth of the frequency-modulated signals is 200 kHz, and the time width is 0.2 ms. Ten ultrasonic tests are performed for each test point, and the time interval between two tests is 0.1 s.

The offline data processing process is as follows:

Algorithms for the offline data processing are realized by scientific calculation software Matlab.

The synthesis/decomposition processes of the gas hydrate are judged by the change curves of the temperature and pressure, and the amount of gas hydrate in the reaction system is calculated according to the temperature and pressure values. The saturation of gas hydrate is calculated by the following formula:

$$S_H = \frac{\left(\frac{P_1}{Z_1 T_1} - \frac{P_2}{Z_2 T_2}\right) \times \frac{V_G}{R} \times M_H}{\rho_H \times V_V}$$

where $S_H$ is the saturation of gas hydrate in the porous medium; $M_H$ is the molar mass of the gas hydrate (122.02 g/mol); $\rho_H$ is the density of the gas hydrate (0.91 g/mL); $V_V$ is the volume of the void of the porous medium (L); $V_G$ is the volume of the gas phase in the reactor (L); T is the system temperature (K); $P_1$ is the initial pressure of the system (MPa); $P_2$ is the system pressure in the synthesis/decomposition processes of the gas hydrate (MPa); R is a gas constant which is 8.314 J/(mol·K); and $Z_1$ and $Z_2$ are gas compression factors in the initial state and in each state of the synthesis/decomposition processes, respectively.

Figure 12:
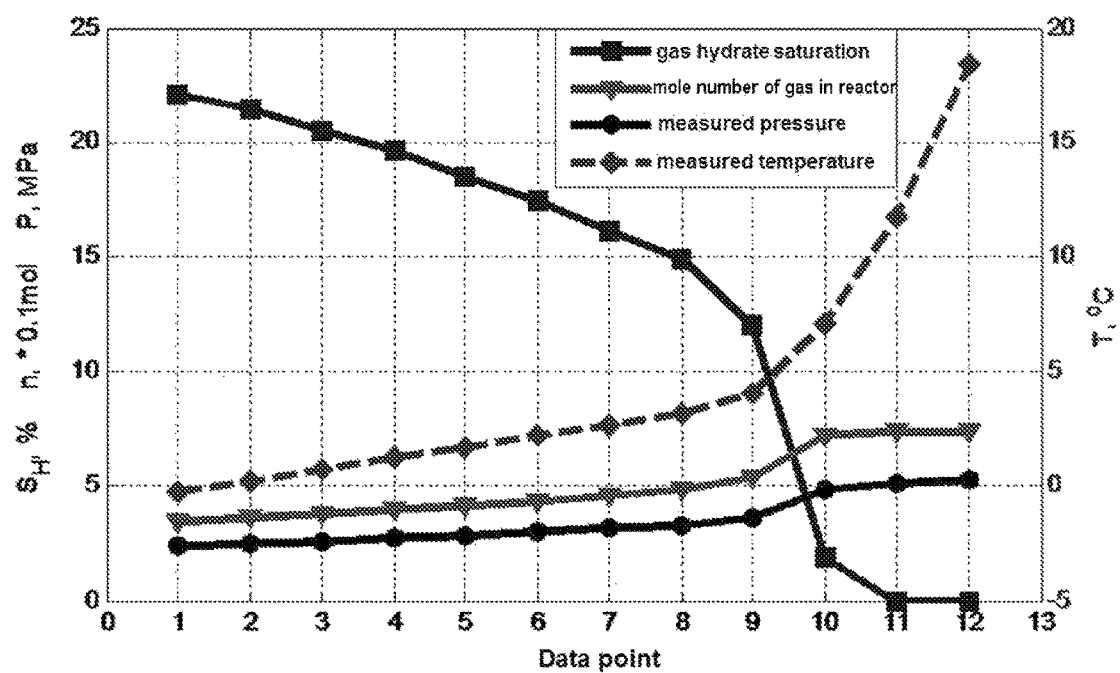
FIG. 12 is a chart showing changes of the saturation of gas hydrate, mole number of gas in the reactor, pressure and temperature at each test point.

FIG. 12 shows changes in the saturation of gas hydrate, mole number of gas in the reactor, and the measured pressure and temperature at each test point in the decomposition process of gas hydrate while raising the temperature.

As shown in FIG. 6, the measurement signals of the electrical sensors are processed and gas hydrate saturation models are established.

In the first step, the measured impedance values are preprocessed, specifically comprising filtering, and characteristic frequency points selection. The filtering can be performed by designing a digital filter by Matlab, and the principle for selecting characteristic frequency points is that frequency points having impedance amplitude changed significantly with the saturation of gas hydrate are selected. In this embodiment, 200 Hz, 2 kHz, 20 kHz and 2 MHz are selected as frequency points.

In the second step, the complex resistivity at each of the selected characteristic frequency points is calculated according to the definition of the complex resistivity and in combination with the structure and size of the reactor. During the calculation, the medium to be tested is a portion of medium within a cylindrical space which takes the area of electrodes as the cross-sectional area and takes the distance between the electrodes as the height.

In the third step, the frequency dispersion of the impedance and the frequency dispersion of the complex resistivity are calculated, respectively, where the frequency dispersion can be the following four forms of parameters: (the impedance (or complex resistivity) value at a high frequency point−the impedance (or complex resistivity) value at a low frequency point)/the impedance (or complex resistivity) value at the high frequency point, (the impedance (or complex resistivity) value at a high frequency point−the impedance (or complex resistivity) value at a low frequency point)/the impedance (or complex resistivity) value at the low frequency point, the impedance (or complex resistivity) value at a high frequency point/the impedance (or complex resistivity) value at a low frequency point), and the impedance (or complex resistivity) value at a low frequency point)/the impedance (or complex resistivity) value at a high frequency point.

In the fourth step, a polynomial fitting (single-input and single-output) is performed between the obtained frequency dispersion parameter of the impedance and the calculated saturation of gas hydrate, and a polynomial fitting (single-input and single-output) is performed between the obtained frequency dispersion parameter of the complex resistivity and the calculated saturation of gas hydrate, so as to obtain a gas hydrate saturation model based on the frequency dispersion of the impedance at the characteristic frequency points and a gas hydrate saturation model based on the frequency dispersion of the complex resistivity of the frequency points, respectively. The impedance values of all the characteristic frequency points selected in the preprocessing process, and the complex resistivity values calculated according to the impedance values, are used as inputs for a multi-dimensional nonlinear mapping which is a three-layer BP neural network in this embodiment, and the calculated saturation of gas hydrate is used as a target output of the three-layer BP neural network, so as to eventually obtain an electrical property fusion model of the saturation of gas hydrate by a typical BP algorithm. The characteristic extraction step is realized by principal component analysis method.

As shown in FIG. 7, the measurement signals of the acoustic sensors are processed and gas hydrate saturation models are established.

In the first step, the acquired acoustic waveforms are processed, comprising filtering, calculating the acoustic wave velocity, acquiring the acoustic wave amplitude and acquiring the acoustic wave frequency. A digital filter is designed by Matlab. Calculating the acoustic wave velocity includes calculating a velocity of longitudinal waves and a velocity of transverse waves, which is done by identifying the arrival time of the first wave of the longitudinal waves and that of the transverse waves in the waveforms and in combination with the size of the reactor. The acoustic wave amplitude refers to the maximum amplitude of corresponding longitudinal waves and the transverse waves in the waveforms. The acoustic wave frequency refers to a dominant frequency of the acoustic waves and is obtained by a certain signal processing method, for example, a frequency spectrum obtained by fast Fourier transform. The frequency point corresponding to the maximum frequency spectrum amplitude is the dominant frequency.

In the second step, property parameters of the acoustic waves in different states are acquired based on the results of calculation in the first step, specifically: (the acoustic wave velocity at a different saturation—the acoustic wave velocity when the saturation of gas hydrate is zero)/the acoustic wave velocity when the saturation of gas hydrate is zero, (the acoustic wave amplitude at a different saturation—the acoustic wave amplitude when the saturation of gas hydrate is zero)/the acoustic wave amplitude when the saturation of gas hydrate is zero, and (the acoustic wave frequency at a different saturation—the acoustic wave frequency when the saturation of gas hydrate is zero)/the acoustic wave frequency when the saturation of gas hydrate is zero.

In the third step, a polynomial fitting (single-input and single-output) is performed between the obtained acoustic wave property parameter of the acoustic wave velocity and the calculated saturation of gas hydrate, a polynomial fitting (single-input and single-output) is performed between the obtained acoustic wave property parameter of the acoustic wave amplitude and the calculated saturation of gas hydrate, and a polynomial fitting (single-input and single-output) is performed between the obtained acoustic wave property parameter of the acoustic wave frequency and the calculated saturation of gas hydrate, so as to obtain a gas hydrate saturation model based on the acoustic wave velocity, a gas hydrate saturation model based on the acoustic wave amplitude and a gas hydrate saturation model based on the acoustic wave frequency, respectively. The three acoustic wave property parameters are used as inputs for a multi-dimensional nonlinear mapping which is a three-layer BP neural network in this embodiment, the calculated saturation of gas hydrate is used as a target output of the three-layer BP neural network, so as to eventually obtain an acoustic property fusion model of the saturation of gas hydrate by a typical BP algorithm. The characteristic extraction step is realized by principal component analysis method.

As shown in FIG. 8, a gas hydrate saturation model based on the data fusion of electrical/acoustic measurement signals is established and applied.

The establishment of the gas hydrate saturation model based on the data fusion of electrical/acoustic measurement signals, i.e., electrical/acoustic property fusion model or model III, is based on the gas hydrate saturation models which are established with respect to the acoustic and electrical measurement signals and which are also called the acoustic sub-model and the electrical sub-model hereinafter. The outputs of the models are combined by a data fusion algorithm, so as to obtain a final gas hydrate saturation output value of the model.

When the gas hydrate saturation model based on the data fusion of electrical/acoustic measurement signals is established, the gas hydrate saturation outputs of the acoustic sub-model and those of the electrical sub-model are used as inputs for the data fusion algorithm, and the calculated saturation of gas hydrate is used as an output. The fusion algorithm is D-S evidence reasoning. Training and parameter correction are performed on the data fusion algorithm by using the calculated saturation of gas hydrate, so that the gas hydrate saturation model based on the data fusion of electrical/acoustic measurement signals (i.e., model III) can be obtained.

Figure 9:
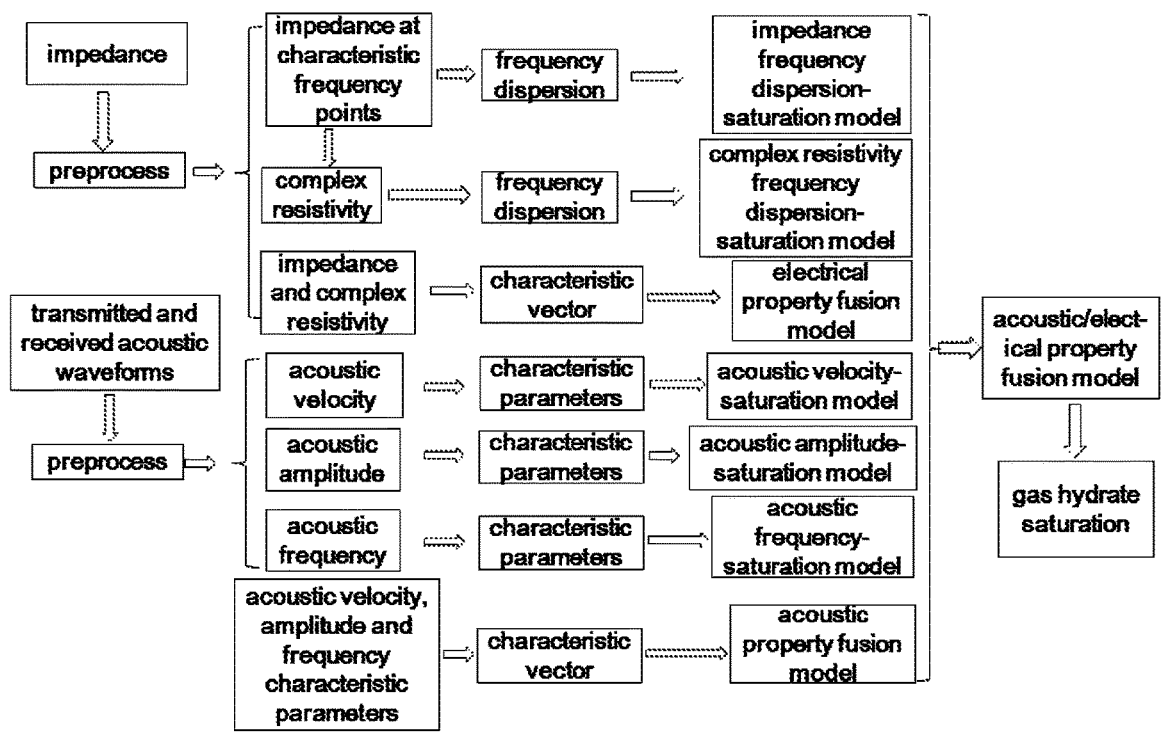
FIG. 9 is an application of an acoustic/electrical property fusion model.

As shown in FIG. 9, when the gas hydrate saturation model based on the data fusion of electrical/acoustic measurement signals is applied, the measurement signals of the electrical sensors and the acoustic sensors are analyzed and processed by the method described above, and the value of the saturation of gas hydrate is eventually output from the acoustic/electrical property fusion model.

The invention claimed is:
1. A test system for a simulation experiment of gas hydrate in a porous medium, mainly comprising a reactor, a sensor system, a hardware interface apparatus and a data processing system; the reactor is used for containing a medium to be tested, the sensor system is mounted inside the reactor, and the sensor system is connected to the data processing system through the hardware interface apparatus; wherein, the sensor system mainly consists of acoustic sensors, electrical sensors, temperature sensors and pressure sensors;

the hardware interface apparatus comprises:

(1) a waveform generator, configured to generate excitation signals required by the sensor system as inputs to the sensor system;

(2) an acoustic/electrical signal data collection module, an impedance measurement circuit and an ultrasonic excitation signal power amplifier; ultrasonic excitation signals are amplified by the ultrasonic excitation signal power amplifier and then used as inputs to the acoustic sensors, outputs of the acoustic sensors are collected by the acoustic/electrical signal data collection module, and the acoustic/electrical signal data collection module collects signal outputs of the electrical sensors through the impedance measurement circuit;

(3) a temperature collection module and a pressure collection module, which collect signals from the temperature sensors and the pressure sensors, respectively;

(4) a multi-path switching module I, configured to switch communication between the waveform generator and the sensor system;

(5) a multi-path switching module II, configured to switch communication between each collection module and the corresponding sensor system; and the data processing system receives and processes data transmitted by each data collection module.

2. The test system for a simulation experiment of gas hydrate in a porous medium according to claim 1, wherein the reactor is of a coaxial double-cylinder structure, an inner cylinder being coaxially arranged inside an outer cylinder, a top cover being provided at an upper end of the outer cylinder for the purpose of sealing, a filter screen being mounted on a bottom of the reactor; a number of holes are correspondingly provided on the inner cylinder and outer cylinder of the reactor in a same radial plane and on a same diameter of the inner cylinder and the outer cylinder, and the acoustic sensors and the electrical sensors are correspondingly mounted within the holes; a number of holes are provided on the bottom of the reactor, and the temperature sensors are mounted in the holes; two holes are provided on the top cover of the reactor for the purpose of receiving a gas pipe II and leading out connecting wires of the sensors, respectively, and a valve and a pressure sensor II are mounted on the gas pipe II; and, two holes are provided on the bottom of the reactor for the purpose of connecting a gas pipe I and a liquid pipe, respectively.

3. The test system for a simulation experiment of gas hydrate in a porous medium according to claim 2, wherein paired acoustic sensors used for transmitting and receiving or paired electrical sensors used for transmitting and receiving are arranged on the inner cylinder and the outer cylinder in a same diameter.

4. The test system for a simulation experiment of gas hydrate in a porous medium according to claim 3, wherein an acoustic sensor and an electrical sensor form an integrated acoustic/electrical sensor, and acoustic/electrical sensors for transmitting and receiving are provided on the inner cylinder and the outer cylinder on a same diameter.

5. The test system for a simulation experiment of gas hydrate in a porous medium according to claim 1, wherein the data processing system receives and processes, through a remote controller, data transmitted by each data collection module.

6. The test system for a simulation experiment of gas hydrate in a porous medium according to claim 4, wherein in an integrated acoustic/electrical sensor, the acoustic sensor is cylindrical and the electrical sensor is ring-shaped; and one end of the acoustic sensor is disposed within the ring of the electrical sensor.

7. The test system for a simulation experiment of gas hydrate in a porous medium according to claim 4, wherein in an integrated acoustic/electrical sensor, the acoustic sensor is cylindrical and the electrical sensor is rectangular; a round hole is formed in the center of the rectangle; and one end of the acoustic sensor is disposed within the round hole of the electrical sensor.

8. The test system for a simulation experiment of gas hydrate in a porous medium according to claim 7, wherein a number of round holes are provided on the rectangle in an axial direction of the reactor; and one end of each of the acoustic sensors is disposed within the round holes of the electrical sensors.

9. A test method for a simulation experiment of gas hydrate in a porous medium, wherein mainly comprising two parts: (1) a procedure of experiment and measurement data acquisition, and (2) a procedure of analyzing and processing measurement signals;

(1) the procedure of experiment and measurement data acquisition comprise:

1) porous medium is filled into a reactor;

2) water and methane gas are fed into the reactor, then the methane gas fully dissolves in the water;

3) the reactor is put in a constant-temperature box, the temperature of the constant-temperature box is set to a certain low temperature to synthesize gas hydrate, and the measurement and control software and the hardware interface apparatus are activated to collect and display data;

4) the temperature of the constant-temperature box is gradually raised at a certain temperature interval to decompose the gas hydrate; when the temperature and pressure in the reactor have become stable after each time of temperature setup, data collection and storage are started; and the data collection and storage is stopped after all data have been stored, and, in step 3) and step 4), the data collection process is as follows: the impedance of the medium to be tested is measured by an electrical sensor pair via an interface circuit; the acoustic wave property parameters of the medium to be tested is measured by an acoustic sensor pair; and the temperature and pressure in the reactor are collected by temperature sensors and pressure sensors;

(2) the procedure of analyzing and processing measurement signals comprises:

5) the amount of gas hydrate in the reactor is calculated according to the temperature and pressure values by the following formula:

$$S_H = \frac{\left(\frac{P_1}{Z_1 T_1} - \frac{P_2}{Z_2 T_2}\right) \times \frac{V_G}{R} \times M_H}{\rho_H \times V_V}$$

6) a model I indicating a quantitative relation between the measurement signals of the electrical sensors and the saturation of gas hydrate is established;

7) a model II indicating a quantitative relation between the measurement signals of the acoustic sensors and the saturation of gas hydrate is established;
8) a model III, indicating a quantitative relation between fused data of the measurement signals of the electrical sensors and the measurement signals of the acoustic sensors, and the saturation of gas hydrate, is established; gas hydrate saturation outputs from the model II obtained in step 7) and the model I obtained in step 6) are used as inputs for a data fusion algorithm, and the calculated saturation of gas hydrate is used as an output to obtain the gas hydrate saturation model based on the data fusion of acoustic/electrical measurement signals, i.e. model III; and
9) the model, indicating the quantitative relation between fused data of the measurement signals of the electrical sensors and the measurement signals of the acoustic sensors, and the saturation of gas hydrate, is applied:
the impedance of the medium to be tested is measured by an electrical sensor pair via an interface circuit, and gas hydrate saturation values I are obtained by a reverse deduction of the model I obtained in step 6);
the medium to be tested are measured by an acoustic sensor pair through pulse signals, and gas hydrate saturation values II are obtained by a reverse deduction of the model II obtained in step 7); and
a value is obtained by fusion algorithm from gas hydrate saturation values, from which a final gas hydrate saturation value III is obtained by a reverse deduction of the model III obtained in step 8).

10. The test method for a simulation experiment of gas hydrate in a porous medium according to claim 9, wherein the step of establishing the model I in step 6) is as follows:
impedance values at a series of frequency points within a certain frequency range and in each state are acquired by the electrical sensors, frequency points having an impedance amplitude changed significantly with the saturation are selected as characteristic frequency points, and the measured impedance values are preprocessed;
complex resistivity at each of the characteristic frequency points is calculated according to the definition of the complex resistivity and in combination with the structure and size of the reactor;
the frequency dispersion of the impedance and the frequency dispersion of the complex resistivity are calculated, respectively;
the above obtained frequency dispersion parameters are respectively performed polynomial fitting with the calculated saturation of gas hydrate, so as to obtain a gas hydrate saturation model based on the frequency dispersion of the impedance at the characteristic frequency points and a gas hydrate saturation model based on the frequency dispersion of the complex resistivity at the characteristic frequency points, respectively;
the impedance values of all the characteristic frequency points and the complex resistivity values calculated according to the impedance values are used as inputs for a multi-dimensional nonlinear mapping, and the calculated saturation of gas hydrate is used as an output of the multi-dimensional nonlinear mapping, so as to eventually obtain an electrical property fusion model of the saturation of gas hydrate by a corresponding learning algorithm.

11. The test method for a simulation experiment of gas hydrate in a porous medium according to claim 9, wherein the step of establishing the model II in step 7) is as follows:
the acquired acoustic waveforms are preprocessed, including filtering, calculating the acoustic wave velocity, acquiring the acoustic wave amplitude and acquiring the acoustic wave frequency;
property parameters of acoustic waves under different gas hydrate saturation conditions are acquired;
the above acoustic wave property parameters are respectively performed polynomial fitting with the calculated saturation of gas hydrate, so as to obtain a gas hydrate saturation model based on the acoustic wave velocity, a gas hydrate saturation model based on the acoustic wave amplitude and a gas hydrate saturation model based on the acoustic wave frequency, respectively;
the above three acoustic wave property parameters are used as inputs for a multi-dimensional nonlinear mapping, the calculated saturation of gas hydrate is used as an output of the multi-dimensional nonlinear mapping, so as to eventually obtain an acoustic property fusion model of the saturation of gas hydrate by a corresponding learning algorithm.

12. The test method for a simulation experiment of gas hydrate in a porous medium according to claim 9, wherein during the data collection in step 3) and step 4), a pair of sensors is switched to work by a multi-path switching module at each measurement.

13. The test method for a simulation experiment of gas hydrate in a porous medium according to claim 9, wherein during the data collection in step 3) and step 4), for the acoustic sensors, the acoustic sensors are excited by a coded excitation technology.

14. The test method for a simulation experiment of gas hydrate in a porous medium according to claim 13, wherein an ultrasonic excitation signal obtained by the coded excitation technology is a single-frequency carrier pulse signal, a frequency-modulated pulse signal, a coded pulse signal, a pulse train signal or a phase encoded continuous-wave signal.

15. The test method for a simulation experiment of gas hydrate in a porous medium according to claim 9, wherein during the data collection in step 3) and step 4), for the electrical sensors, the excitation signal performs frequency sweeping excitation on every test point within a certain frequency range by a voltage signal having sine waveforms with a certain amplitude, frequency and DC bias; the amplitude is 0.01 V-5V and the frequency is 0.01 Hz -100 MHz.

16. The test method for a simulation experiment of gas hydrate in a porous medium according to claim 12, wherein during the data collection in step 3) and step 4), for the acoustic sensors, the acoustic sensors are excited by a coded excitation technology.

17. The test method for a simulation experiment of gas hydrate in a porous medium according to claim 10, wherein the step of establishing the model II in step 7) is as follows:
the acquired acoustic waveforms are preprocessed, including filtering, calculating the acoustic wave velocity, acquiring the acoustic wave amplitude and acquiring the acoustic wave frequency;
property parameters of acoustic waves under different gas hydrate saturation conditions are acquired;
the above acoustic wave property parameters are respectively performed polynomial fitting with the calculated saturation of gas hydrate, so as to obtain a gas hydrate saturation model based on the acoustic wave velocity, a gas hydrate saturation model based on the acoustic wave amplitude and a gas hydrate saturation model based on the acoustic wave frequency, respectively;

the above three acoustic wave property parameters are used as inputs for a multi-dimensional nonlinear mapping, the calculated saturation of gas hydrate is used as an output of the multi-dimensional nonlinear mapping, so as to eventually obtain an acoustic property fusion model of the saturation of gas hydrate by a corresponding learning algorithm.

18. The test method for a simulation experiment of gas hydrate in a porous medium according to claim 17, wherein during the data collection in step 3) and step 4), for the acoustic sensors, the acoustic sensors are excited by a coded excitation technology.

19. The test method for a simulation experiment of gas hydrate in a porous medium according to claim 18, wherein an ultrasonic excitation signal obtained by the coded excitation technology is a single-frequency carrier pulse signal, a frequency-modulated pulse signal, a coded pulse signal, a pulse train signal or a phase encoded continuous-wave signal.

20. The test method for a simulation experiment of gas hydrate in a porous medium according to claim 17, wherein during the data collection in step 3) and step 4), for the electrical sensors, the excitation signal performs frequency sweeping excitation on every test point within a certain frequency range by a voltage signal having sine waveforms with a certain amplitude, frequency and DC bias; the amplitude is 0.01 V-5V and the frequency is 0.01 Hz -100 MHz.

* * * * *